United States Patent
Rajasekharan et al.

(10) Patent No.: US 11,235,021 B2
(45) Date of Patent: Feb. 1, 2022

(54) AMPHIPHILIC ANTIMICROBIAL HYDROGEL

(71) Applicant: AMFERIA AB, Gothenburg (SE)

(72) Inventors: Anand Kumar Rajasekharan, Gothenburg (SE); Saba Atefykta, Gothenburg (SE); Martin Andersson, Mölndal (SE)

(73) Assignee: AMFERIA AB, Gothenburg (SE)

( * ) Notice: Subject to any disclaimer, the term of this patent is extended or adjusted under 35 U.S.C. 154(b) by 0 days.

(21) Appl. No.: 16/755,275

(22) PCT Filed: Oct. 1, 2018

(86) PCT No.: PCT/SE2018/051002
§ 371 (c)(1),
(2) Date: Apr. 10, 2020

(87) PCT Pub. No.: WO2019/074422
PCT Pub. Date: Apr. 18, 2019

(65) Prior Publication Data
US 2020/0237857 A1    Jul. 30, 2020

(30) Foreign Application Priority Data
Oct. 13, 2017  (SE) ................... 1751277-3

(51) Int. Cl.
*A61K 38/10*    (2006.01)
*A61P 31/04*    (2006.01)
*A61K 9/06*     (2006.01)

(52) U.S. Cl.
CPC ............... *A61K 38/10* (2013.01); *A61K 9/06* (2013.01); *A61P 31/04* (2018.01)

(58) Field of Classification Search
None
See application file for complete search history.

(56) References Cited

U.S. PATENT DOCUMENTS

2007/0254006 A1*  11/2007  Loose ............... A61L 31/16
                                              424/423
2016/0051724 A1   2/2016  Schmidtchen et al.

FOREIGN PATENT DOCUMENTS

WO    WO-2012033450 A1 *  3/2012  ............. A61P 31/00

OTHER PUBLICATIONS

F. Costa, Acta Biomaterialia, (20110000), vol. 7, pp. 1431-1440.
He, W. et al., "Mesoscopically Ordered Bone-Mimetic Nanocomposites", Adv. Mater., vol. 27, pp. 2260-2264.

* cited by examiner

*Primary Examiner* — Melissa S Mercier
(74) *Attorney, Agent, or Firm* — Duane Morris LLP; Gregory M. Lefkowitz; Brandon A. Chan

(57) ABSTRACT

A solid antimicrobial hydrogel comprising a first amphiphilic component. The first amphiphilic component, in its chemically cross-linked state, being a lyotropic liquid crystal and having an ordered nanostructure of hydrophobic and hydrophilic domains, the composition further comprising an antimicrobial agent being covalently attached to at least one of the hydrophilic or hydrophobic domains.

21 Claims, 11 Drawing Sheets

Specification includes a Sequence Listing.

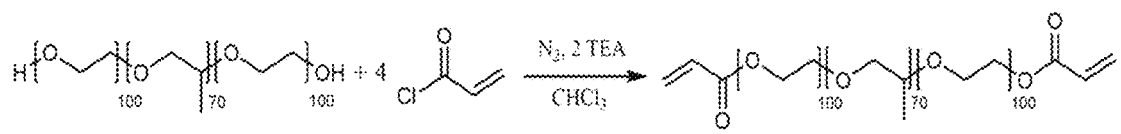
Fig. 1
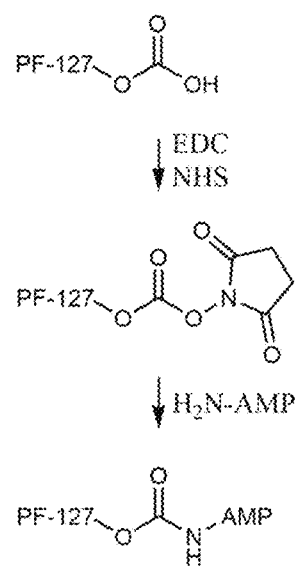
Fig. 2
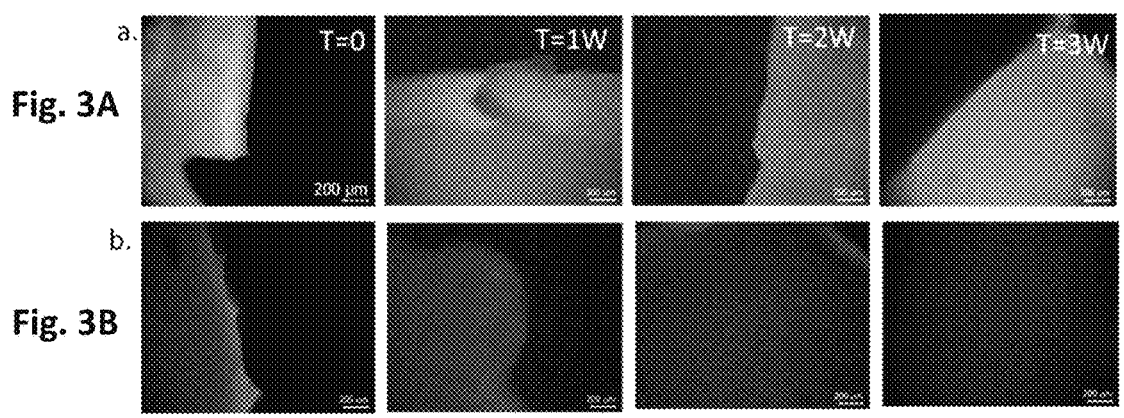
Fig. 3A
Fig. 3B

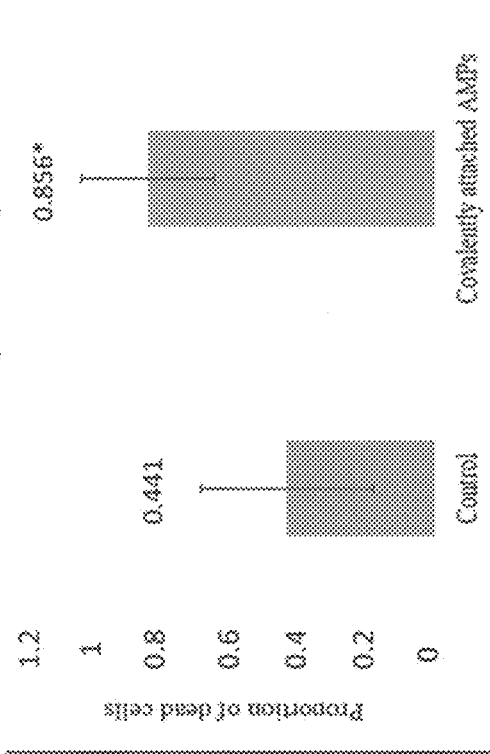
Fig. 8A LIVE/DEAD staining of *S. epidermidis*
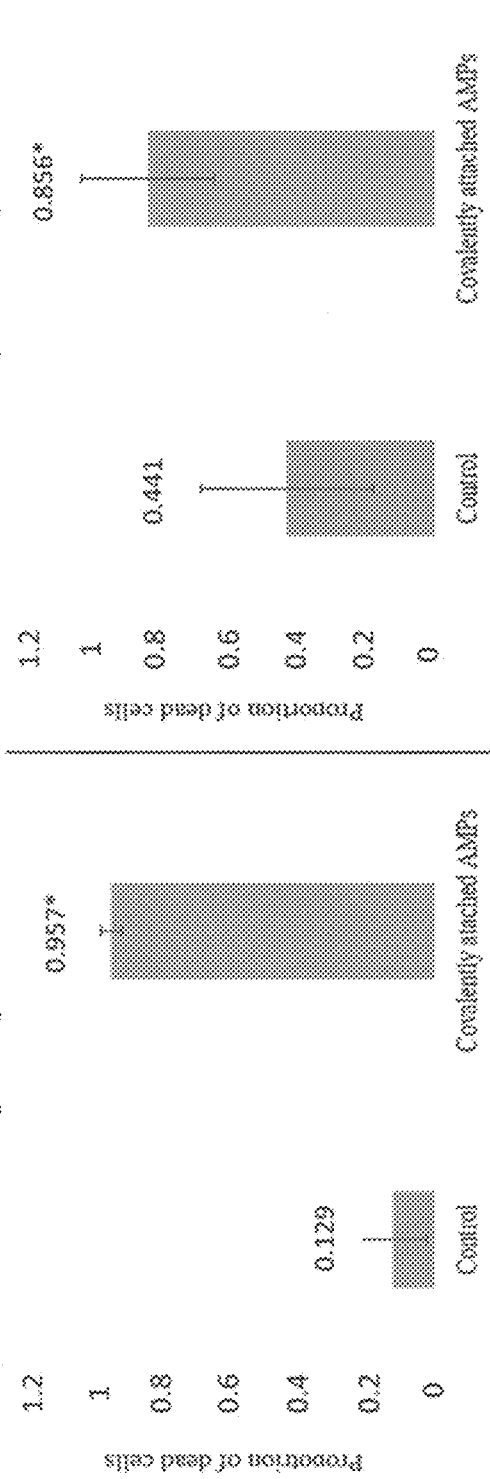
Fig. 8C
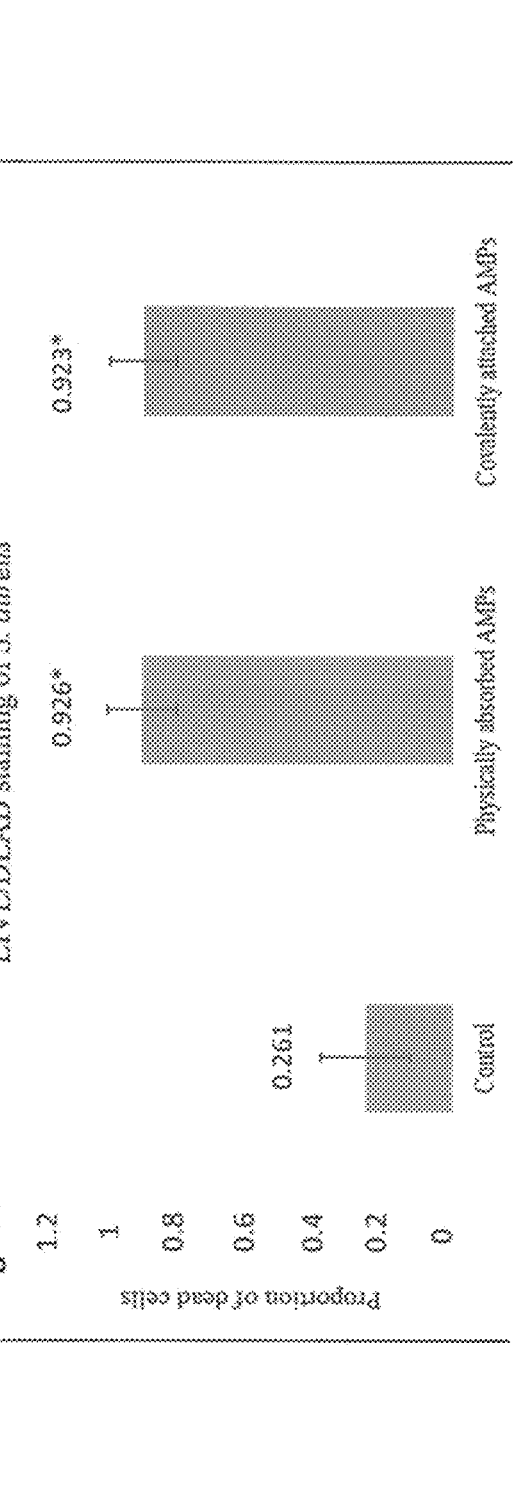
Fig. 8B LIVE/DEAD staining of *P. aeruginosa*
LIVE/DEAD staining of *S. aureus*

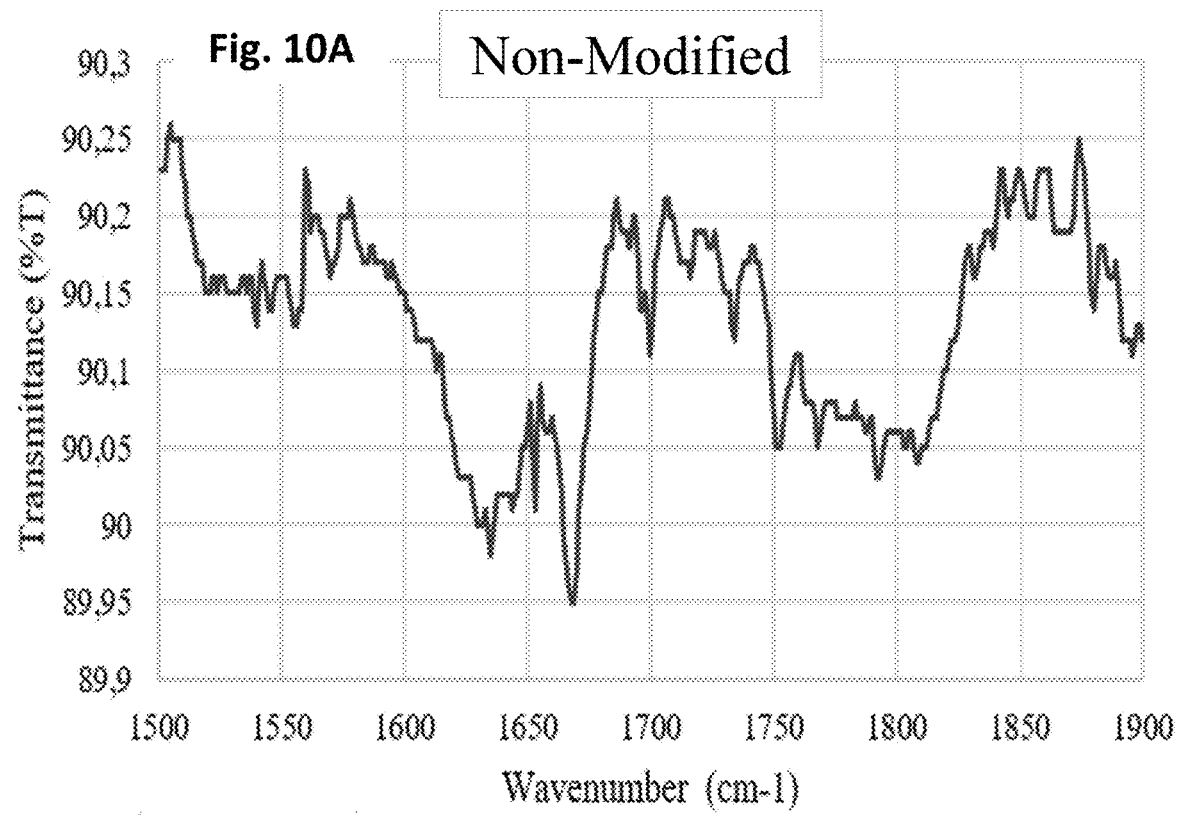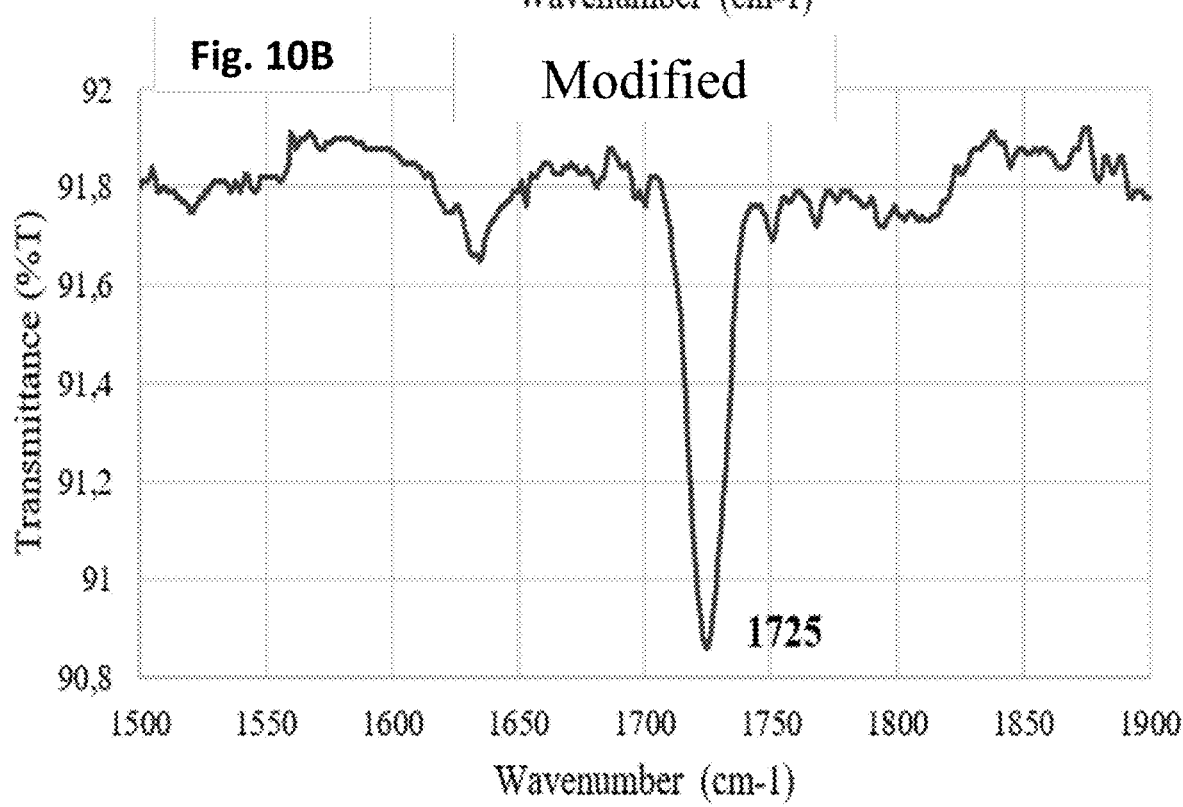

AMPHIPHILIC ANTIMICROBIAL HYDROGEL

FIELD OF THE INVENTION

The present disclosure relates to antimicrobial hydrogels. Specifically, it relates to an antimicrobial hydrogel comprising a first amphiphilic component and an antimicrobial agent covalently attached thereto.

BACKGROUND OF THE INVENTION

Wound infection involving the skin or tissues in the vicinity of a wound interferes with the healing process and may cause systemic illnesses. Today, antibiotic therapy is the most common treatment for treating wound infection. Over many years, such antibiotic therapy routines have not only been shown to cause systemic side effects to the patients but has also resulted in a rapid increase in severe infections caused by antibiotic resistant bacteria.

A number of wound dressings are available today that are intended to reduce or eliminate infections. However, the ever-increasing problem of antibiotic resistance has pushed the need for new and advanced wound dressings. Many commercially available wound dressings such as Mepilex® or Mepilex-Ag® (marketed by Mölnlycke Health Care) incorporate soft superabsorbent dressing layers comprising silver as the antimicrobial agent. The silver is released into the wound and kills the microbes by damaging the cell wall or inhibiting the microbe from reproduction. Numerous other wound dressings incorporate antimicrobial molecules such as chlorhexidine or conventional antibiotic drugs such as penicillin are used to prevent bacterial adhesion or infection at the wound site. However, the above compounds are limited in use due to their limited spectrum of activity, cytotoxicity to human cells and the possibility of development of antimicrobial resistance in short period.

Much of the recent work has focused on the covalent immobilization of antimicrobial compounds such as silver sulphadiazine, antibiotic phenol derivatives, chlorhexidine and quaternary ammonium polymers to substrates for use in wound dressings (F. Costa et. al., *Acta Biomaterialia* 7 (2011) 1431-1440). Covalent immobilization of these compounds stops the molecules from leaching out into the biological environment while preventing infections from developing at the injury or wound site. The active compounds are attached to the rest of the wound dressing which can be in the form of fibres, hydrogels or commercially available flexible plastics. Although covalent attachment limits the quantity of antimicrobial substances in the dressing, it still poses a risk for cytotoxicity of the epithelial human cells present in and around the wound site.

Therefore, cationic antimicrobial polymers such as antimicrobial peptides (AMPs) as alternative drugs, are receiving increased attention especially in the treatment of skin wounds.

However, problems arise when AMPs are used as therapeutic agents in wound dressings, which have traditionally focused on release or leaching of physically adsorbed AMPs to perform the desired function. Two major drawbacks exist in the aforementioned approach. AMPs are generally peptide molecules where the amide bond is the predominant linkage between different amino acids. The amide bonds are susceptible to degradation from enzymes in the biological environment thus calling for the need to increase the number of AMPs, often in the micro to milligram level to function which in-turn increases the cost of the device. This limit the use of AMPs as functional therapeutic agents in medical devices.

US 2007/0254006 A1 discloses a substrate which may be a dextran hydrogel to which AMPs may be tethered. The dextran hydrogel of US 2007/0254006 A1 has a hydrophilic and randomly cross-linked structure. AMPs tethered to such a structure may be prone to degradation. Furthermore, AMPs can only be provided attached to the tethers and not absorbed in to the dextran hydrogel.

Improved materials having antimicrobial properties are therefore desirable.

SUMMARY OF THE INVENTION

Accordingly, the present invention preferably seeks to mitigate, alleviate or eliminate one or more of the above-identified deficiencies in the art singly or in any combination and solves at least the above mentioned problems by providing an antimicrobial hydrogel comprising a first cross-linkable amphiphilic component, said first amphiphilic component having, in its chemically cross-linked state, an ordered nanostructure of hydrophobic and hydrophilic domains, the composition further comprising an antimicrobial agent being covalently attached to at least one of the hydrophilic or hydrophobic domains.

A device comprising an antimicrobial hydrogel is also provided.

A method of producing an antimicrobial hydrogel is further provided.

Further advantageous embodiments are disclosed in the appended and dependent patent claims.

BRIEF DESCRIPTION OF THE DRAWINGS

These and other aspects, features and advantages of which the invention is capable will be apparent and elucidated from the following description of embodiments of the present invention, reference being made to the accompanying drawings, in which FIG. 1 is a synthesis scheme of diacrylate modified Pluronic® triblock copolymer where X and Y refer to the number of PEO and PPO groups.

FIG. 2 shows the reaction scheme of the covalent attachment of antimicrobial peptides to diacrylate modified Pluronic triblock copolymer F-127 by EDC/NHS activation.

FIG. 3 shows fluorescent microscopy images of 5(6) carboxyfluorescein tagged RRPRPRPRPWWWW-NH$_2$. FIG. 3*a* (upper row) shows, the tagged peptide covalently immobilized onto DA-F127 normal micellar cubic hydrogels prepared according to the experimental section and FIG. 3*b* (lower row), shows tagged peptide physically absorbed onto DA-F127 normal micellar cubic hydrogels, that is, not covalently immobilized. All samples treated in 50% ethanol for a maximum of 3 weeks.

FIG. 5 shows a zone inhibition test of the antimicrobial hydrogel vs control samples.

FIG. 7 shows live/dead images of various biofilms formed on a control amphiphilic hydrogel (leftmost image) and an antimicrobial amphiphilic hydrogel according to an aspect (rightmost image).

FIG. 8 shows a quantitative analys of the proportion of dead bacterial cells on the surface of the hydrogels in FIG. 7. The proportion of dead cells was calculated using an image analysis macro according to the formula: (dead cells÷(dead cells+alive cells)) to account for differences in biofilm growth. FIG. 8a shows S. epidermis. FIG. 8b shows P. aeruginosa. FIG. 8c includes a proportion of dead cells in a hydrogel where AMPs were physically absorbed and not covalently attached. The astreix (*) indicates a significant difference compared to the control sample at a 95% confidence level.

FIG. 11 shows the results from a storage stability test in phosphate buffered saline (PBS).

DETAILED DESCRIPTION

Figure 4A:
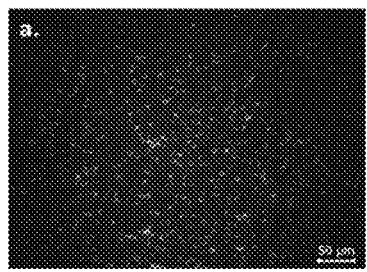
FIG. 4 shows live/dead images of *S. epidermidis* biofilms formed onto: a, amphiphilic hydrogels prepared according to the experimental section but without any AMP; b, Amphiphilic hydrogels with physically absorbed AMPs, that is, not covalently attached AMPs; and c, amphiphilic antimicrobial hydrogels according to an aspect where the AMPs have been covalently immobilized on the amphiphilic hydrogel. The bacteria are stained with SYTO® 9 and propidium iodide. The live bacteria appear green and the dead bacteria appear red.

The following description of the present invention describes an improved antimicrobial hydrogel. The antimicrobial hydrogel comprises a first cross-linkable amphiphilic component. In its cross-linked state, the amphiphilic component results in a hydrogel comprising an ordered structure of hydrophilic and hydrophobic domains. The antimicrobial hydrogel further comprises an antimicrobial agent covalently bonded to the repeating hydrophilic and/or hydrophobic domains of the cross-linked hydrogel.

The repeating ordered nanostructure comprises repeating and alternating hydrophobic-hydrophilic domains. The morphology and specific structure of the hydrophobic-hydrophilic domains is discussed below. The hydrogel comprises an ordered and repeating nanostructure throughout the hydrogel, that is, not only on the surface of the hydrogel. The cross-linked hydrogel is solid. Intermolecular cross-linking irreversibly locks the ordered structure and results in a hydrogel which has a high integrity and is mechanically resilient.

The antimicrobial hydrogel is especially suitable for wound care applications due to the ordered and repeating nanostructure leading to an ordered and repeating provision of antimicrobial agents on the skin or wound surface. Furthermore, antimicrobial agents are better immobilized leading to better long-term performance.

The hydrogel may be considered to form a substrate on to which antimicrobial agents can be immobilized. The hydrogel is, in its cross-linked state, self-supporting and three-dimensional. Generally, the hydrogel is substantially non-degrading in physiological conditions. That is, the hydrogel is non-biodegradable, it is substantially not degraded by chemical or enzymatic conditions found in the relevant in vitro and in vivo conditions. For example, the hydrogel is not degraded in the presence of blood, sweat, urine or other biological fluids. Furthermore, the hydrogel is substantially non-degrading, that is, it is stable and remains a solid, in relatively low or high pH environments.

The hydrogel may form a first substantially uniform layer to which antimicrobial agents are covalently attached. Antimicrobial agents may be covalently attached to at least the repeating hydrophilic domains of the hydrogel throughout the layer. They may be provided within the layer, and not only on the surface of the hydrogel. This is a significant improvement compared to techniques of surface modification of a hydrogel or other substrate which lead to only surface immobilization of antimicrobial agents.

The repeating and ordered structure of hydrophilic and hydrophobic domains is ordered on at least the nanoscale, and as will be discussed further below, may be ordered on a larger, micro or macro scale depending on production techniques. The terms ordered and repeating relate to the hydrogel having a defined periodicity. As opposed to hydrogels based on carbohydrates, polysaccharides or other non-amphiphilic molecules the nanostructure of the hydrogel as described herein has an ordered and repeating nanostructure and is not randomly cross-linked. The hydrogel is amphiphilic. After cross linking, the amphiphilic hydrogel is a chemically cross-linked amphiphilic hydrogel.

The ordered and repeating nanostructure results in antimicrobial agents covalently bonded to the hydrogel having a defined orientation. If the antimicrobial agents themselves are amphiphilic then the antimicrobial agent is furthermore more effectively immobilized on the surface of, and within, the hydrogel. The amphiphlicity of the hydrogel also allows the absorption of both aqueous and non-aqueous solutions.

As stated above, as opposed to a hydrogel having a surface treatment to define a surface chemistry, the hydrogel of the present disclosure has a repeating and ordered nanostructure both on the surface and within the bulk of the hydrogel. This leads to improved immobilization of antimicrobial agents both on the surface and within the hydrogel.

The antimicrobial hydrogel may be formed by the chemical cross-linking of organic amphiphilic materials such as cross-linkable copolymers, cross-linkable surfactants, cross-linkable proteins, cross-linkable peptides and cross-linkable lipids. Cross-linkable as used herein refers to the covalent linkage of molecules to each other using reactive chemical groups present on the molecules. The chemical cross-linking process can be catalysed using light such as ultraviolet light, heat, or other chemical catalysts such as enzymes. The covalent cross-linking of the hydrogel is non-reversible. The covalent cross-linking will not degrade or disintegrate at increased temperatures. The covalent cross-linking is also stable towards pH variations.

The first amphiphilic component of the hydrogel may be a cross-linkable amphiphilic polymer. A typical and suitable amphiphilic material is a diacrylate modified poloxamer, such as, polyethylene oxide-polypropylene oxide-polyethylene oxide (DA-PEO$_x$-PPO$_y$-PEO$_x$-DA, where x and y refer to the number of PEO and PPO groups present respectively) as described in the experimental section below. Specifically, the amphiphilic material may be the amphiphilic tri-block co-polymers, polyethylene oxide(100)-polypropylene oxide(70)-polyethylene oxide(100) (Pluronic® F127-BASF Corporation), polyethylene oxide(30)-polypropylene oxide(70)-polyethylene oxide(30) (Pluronic® P123-BASF Corporation).

As stated above, the amphiphilic component may be a diacrylate derivative of a tri-block copolymer thus enabling the copolymer to be chemically cross-linked. A process for diacrylate modification is provided in the experimental section below. The modification may be performed via the reaction of a triblock amphiphilic copolymer with acryloyl chloride to form a diacrylate derivative. Other methods of forming cross-linkable amphiphilic polymers may be possible such as forming methacrylate derivatives or via carboxylic-amine bridges.

The cross-linkable amphiphilic polymer may, in the presence of water, self-assemble to form ordered nanostructures called lyotropic liquid crystals (LLC). In its cross-linked form, that is, after cross-linking, the hydrogel may be considered a chemically cross-linked lyotropic liquid crystal (LLC). The cross-linking of the amphiphilic polymer may be considered to form a polymerized lyotropic liquid crystal (PLLC) having a well-defined structure.

A non-solid cross-linked hydrogel may have a structure of spherical micellar aggregates in size range of 2-100 nm arranged randomly throughout the hydrogel called as a normal micellar system, denoted in shorthand as L$_1$. Such a normal micellar hydrogel may comprise from about 1% to about 19% (% wt) amphiphilic polymer, and from about 99% to about 81% (% wt) water. Generally, this system does not form a cross-linked solid gel, however in certain cases such as between the range of 15-19% (% wt) amphiphilic polymer concentration, the system can exist as a crosslinked solid with very soft and pliable mechanical features.

The hydrogel may have a structure of spherical micellar aggregates in the size range 2-100 nm arranged in a lyotropic liquid crystal, cubic shaped, ordered arrangement known as a normal micellar cubic system, denoted in shorthand as I$_i$, with a primitive arrangement (P . . . ) or body centered (B . . . ) arrangement or a face centered (F . . . ) arrangement of micellar structures in a cubic lattice. An example of a normal micellar cubic structure with an Im3m crystal symmetry may comprise from about 20% to about 65% (% wt) amphiphilic polymer and from about 80% to about 35% (% wt) water. Another example composition to obtain a normal micellar cubic system with primitive arrangement of a micellar structures in a cubic lattice is 65% (% wt) water, 10% (% wt) butanol and 25% (% wt) amphiphilic polymer.

The hydrogel may have a structure of spherical micellar aggregates in the size range 2-100 nm arranged in a lyotropic liquid crystal, bicontinuous cubic shaped, ordered arrangement known as a micellar cubic system with Pn3m crystal structure. Such a bicontinous micellar cubic system with Pn3m crystal structure may comprise from about 25% to about 65% (% wt) amphiphilic polymer and from about 75% to about 35% (% wt) water. Another example composition to obtain such a LLC structure is 33-38% (% wt) water and the rest composed of an amphiphilic species or amphiphilic polymer.

The hydrogel may have a structure of spherical micellar aggregates in the size range 2-100 nm arranged in a lyotropic liquid crystal, bicontinuous cubic shaped, ordered arrangement known as a micellar cubic system with Ia3d crystal structure. An example composition to obtain such a LLC structure is 13-32% (% wt) water and the rest composed of the amphiphilic species or amphiphilic polymer.

The hydrogel may have a structure of cylindrical micellar aggregates with diameter of cylinders in the size range of 2-100 nm arranged in an ordered lyotropic liquid crystal, hexagonal geometry called as a normal hexagonal system In such a normal hexagonal system, the amphiphilic polymer may be present in from about 30% to about 80% (% wt) and water may be present in from about 60% to about 20% (% wt), with or without minor amounts of organic solvents. Such a normal micellar hexagonal system may comprise from about 35% to about 40% (% wt) amphiphilic polymer, about 50% (% wt) water, and from about 10% to about 15% (% wt) organic solvent.

The antimicrobial hydrogel may also have a chemically cross-linked, ordered nanostructure of the following structures with a neutral geometry and zero curvature; sheet-like micellar aggregates with distance between adjacent sheets is in the range of 2-100 nm, arranged as lyotropic liquid crystal, lamellar geometry called as a lamellar system. Such a lamellar system might comprise anywhere between 20-80% (% wt) amphiphilic molecule, 15-60% (% wt) aqueous solution and 0-25% (% wt) organic solvents such as butanol. An example composition of to obtain a lamellar LLC is 20% amphiphilic polymer, 55% (% wt) water and 25% (% wt) organic solvent such as butanol.

Micellar and lyotropic liquid crystal nanostructures of the antimicrobial hydrogel may comprise aqueous liquids such as water as the continuous domain and hydrophobic parts confined within the micellar aggregates. The micellar and lyotropic liquid crystal nanostructure may comprise an aqueous liquid such as water confined within the micellar aggregates and a hydrophobic continuous domain. Aqueous liquids include, but are not limited to, water, salt solutions, blood, sweat and other possible biological fluids. In its fully wet, also known as swollen state, the antimicrobial hydrogel can absorb up to 3 to 4 times its own weight of aqueous liquids. A fully wet/swollen state refers to the original concentration (by weight) of the hydrogel of 20-90% aqueous solution and 10-80% amphiphilic organic molecules, depending on the type of crosslinked LLC structure the hydrogels possesses. In its fully dry state the hydrogel uniformly contains less than 10% aqueous solution by weight, and more usually less than 5% aqueous solution by weight, in which case it may absorb up to 8 to 10 times aqueous solution of its own weight. Tables 2 and 3 detail the liquid absorption behaviour of the antimicrobial hydrogel. Following liquid absorption, the antimicrobial hydrogel swells and changes in size. However, the shape and geometry of the hydrogels is substantially retained.

Due to the amphiphilicity of the antimicrobial hydrogel it may also absorb hydrophobic liquids. As shown in Table 2 in the experimental section, in the presence of the hydrophobic solvent chloroform, the fully-dry hydrogel can absorb hydrophobic liquid, such as chloroform, up to 20 to 30 times its own weight. As above, a fully dry state refers to the concentration of the hydrogel of less than 5% aqueous solution and greater than 95% amphiphilic organic molecules by weight.

The liquid absorption properties of the hydrogels can be tailored to absorb more or less water or hydrophobic liquids. This can be achieved by using amphiphilic molecules of different ratios of chain lengths in hydrophilic to hydrophobic groups to form the hydrogel. For example, amphiphilic block copolymer DA-$PEO_x$-$PPO_y$-$PEO_x$-DA, where x and y refer to the number of PEO and PPO, groups can possess more or less PEO or PPO groups. Higher amounts of PEO groups than PPO groups may result in a hydrogel with high water absorption capacity, up to 3 to 8 times its own initial weight. Conversely, a hydrogel with more PPO groups than PEO groups absorbs less water approximately, 0.5-1.5 times its initial weight. This effect is exemplified in Table 3 in the experimental section of for liquid absorption properties of hydrogel materials formed from DA-$PEO_{100}$-$PPO_{70}$-$PEO_{100}$-DA and hydrogel materials formed from DA-$PEO_{30}$-$PPO_{70}$-$PEO_{30}$-DA.

The antimicrobial agent is covalently bonded to the repeating hydrophilic and/or hydrophobic domains. In the antimicrobial hydrogel, there is a plurality of antimicrobial molecules each of which is covalently bonded to at least a portion of the repeating and periodic hydrophilic and/or the hydrophobic domains.

Greater than 10%, such as greater than 50%, or greater than 90% of the antimicrobial agent present in the hydrogel may be covalently attached to the hydrogel. This results in greater stability and reduced leaching of antimicrobial agent from the hydrogel.

The antimicrobial agent may be an amphiphilic antimicrobial agent. That is, the antimicrobial molecule may have a hydrophilic region and a hydrophobic region. The antimicrobial agent may be selected such that it ruptures the bacterial cell wall via electrostatic forces. The antimicrobial agent may be an antimicrobial polymeric molecule such as polymeric biocides or an antimicrobial peptide (AMP). AMPs generally disrupt or inhibit microbial growth and proliferation by damaging the microbes' cell membranes. AMPs are generally amphiphilic. AMPs are generally short chain peptides, i.e. consisting of 1-25 amino acids, and molecular weights between 10-25 kDa. AMPs can be linear chained AMPs, branched AMPs and/or cyclic AMPs. They generally possess a net positive charge and possess both hydrophilic and hydrophobic regions. It is known that the positively charged, amphiphilic structure of AMPs enables the peptide to penetrate the negatively charged bacterial membrane. The compromised cell wall leads to cell death. The amphiphilic nature of AMPs in combination with the ordered and repeating nanostructure of the hydrogel leads to orientation and higher immobilization of AMPs. That is, the AMPs do not separate or release from the underlying hydrogel. This results in the antimicrobial hydrogel being a non-leachable substrate for the antimicrobial agents. An AMP may be covalently attached to both a hydrophilic domain and a hydrophobic domain of the amphiphilic hydrogel. An AMP may be covalently attached to adjacent hydrophilic and hydrophobic domains. The N-terminus of an AMP may be covalently attached to the hydrophobic domains of the hydrogel. The C-terminus of an AMP may be covalently attached to the hydrophilic domains of the hydrogel.

An AMP may be both covalently attached to the amphiphilic hydrogel and physically absorbed in to the hydrogel. As is shown by the right-most image in FIG. 3B even after 3 weeks of washing in 50% ethanol the amphiphilic hydrogel does not release all of the physically absorbed fluorescent tagged AMP. This is due to the amphiphilicity of the hydrogel and the interaction of the AMP with the hydrophilic and hydrophobic domains of the hydrogel. This results in increased antimicrobial performance and long-term stability during use.

The antimicrobial agent may be silver (Ag). For example, the antimicrobial agent may be a silver nanoparticle immobilized within or on the repeating and ordered hydrophilic and/or hydrophobic domains of the hydrogel. As discussed above, silver has the disadvantage of increased toxicity to mammalian cells, however, it is also generally a lower cost antimicrobial agent in comparison to an AMP.

It would not be apparent to the skilled person that carboxyl groups would be present in the amphiphilic hydrogel. Therefore, there is no reason as such to attempt to covalently attach an AMP to the amphiphilic hydrogel, without additional modifications to the hydrogel. However, as is shown in FIGS. 10B-E carboxyl groups are present in the amphiphilic hydrogel and is achieved during the crosslinking process of the hydrogel.

The immobilization is generally achieved via the covalent bonds between carboxyl groups on the hydrophilic domains of the hydrogel. In the case of the antimicrobial agent being an antimicrobial peptide, strong amide bonds are formed between the AMP and the repeating hydrophilic domains of the hydrogel. As disclosed in the experimental section the AMP may be covalently bonded to the hydrogel via 1-Ethyl-3-(3-dimethylaminopropyl) carbodiimid (EDC)-N-hydroxysuccinimide (NHS) activation of the carboxyl groups present on the hydrophilic domains of the hydrogel. The reaction scheme for such covalent attachment of AMPs via EDC/NHS activation can be seen in FIG. 2. As can be seen in the experimental section, AMPs or other antimicrobial agents may furthermore be physically absorbed in to the hydrogel, however, in such a case there is no covalent bonding of the antimicrobial agent to the hydrophilic or hydrophobic regions of the hydrogel. Non-covalently bonded antimicrobial agents are, however, prone to relatively faster degradation and leaching/release from the hydrogel.

The AMP, or other amphiphilic antimicrobial agent, has a hydrophobic region which interacts with the ordered and repeating hydrophobic regions of the hydrogel. This leads to improved orientation and improved immobilization of the antimicrobial agent. Stability and resistance to degradation of the AMPs is thus increased, while decreasing or eliminating the release of AMPs in to the surrounding environment, due to the hydrogel having ordered and repeating hydrophilic and hydrophobic domains. Such an architecture can improve the stability and activity of AMPs from few hours to upto 2 days or longer according to the results in the experimental section.

As shown in the experimentation section below, the antimicrobial hydrogel is capable of killing up to 99.99% of gram-positive and gram-negative bacteria. Without being bound by theory, a further benefit is that the hydrophilic domains of the antimicrobial hydrogel are capable of attracting the negatively charged bacteria and therein effectively killing them. In wound care applications, this may also lead to the removal of dead and/or attached bacteria via removal of a wound dressing comprising the antimicrobial hydrogel. The experimental results for gram-positive and gram-negative bacteria suggest that the antimicrobial hydrogel is also capable of killing drug resistant strains of bacteria such as MRSA and multi-drug resistant (MDR) E-coli.

As shown in the experimental section, the antimicrobial peptide may be one or more of the following; RRPRPR-PRPWWWW-NH2 (RRP9W4N, Red Glead Discovery AB, Lund, Sweden), RRPRPRPRP-NH2 (RRP9N, Red Glead Discovery AB, Lund, Sweden), RRPRPRPWWWWRP-NH2 (RRP7W4RPN, Red Glead Discovery AB, Lund, Sweden), RRPRPWWRPWWRP-NH2 (RRP5W2 RPW2RPN, Red Glead Discovery AB, Lund, Sweden). Sequences for RRP9W4N, RRP9N, are provided in WO 2012/033450 A1. Sequences for RRP7W4RPN (SEQ ID NO:1) and RRP5W2RPW2RPN (SEQ ID NO: 2) are provided together with this application. The antimicrobial peptide may be an antimicrobial peptide comprising less than 20 amino acids which comprises an amino acid sequence having at least 90%, such as 95%, identity to the amino acid sequence RRPRPRPRP (sequence provided in WO 2012/033450 A1), and optionally, a stretch of at least three consecutive tryptophan of phenylalaline residues appended to either the C- or N-terminus, or therebetween. The antimicrobial peptide may comprise an N-terminal amidation. The antimicrobial peptide may be an antimicrobial peptide comprising a stretch of at least one, such as at least three, hydrophobic amino acids, such as phenylaline, or tryptophan residues, forming a hydrophobic region. The hydrophobic region allows for intereaction with the hydrophobic regions of the hydrogel. However, other antimicrobial peptides may be suitable for use as the antimicrobial agent.

The antimicrobial agent may be a synthetically derived AMP as those in the preceding paragraph or biologically derived. Biologically derived AMPs can be derived from a kininogen proteins, proline and arginine rich end leucine rich repeat protein (PRELP), growth factor proteins, coagulation system proteins, complement factor C3a, von Willebrand factor, vitronectin, superoxide dismutase, prion proteins, protein C inhibitor, fibronectin, laminin, chemokines, and histidine rich glycoprotein. Some examples of biologically derived AMPs are human cathelicidin derived LL-37 peptide and Omiganan pentahydrochloride. All these peptides can be potentially incorporated in the hydrogel as covalently attached or physically absorbed. Alone or together with other peptides.

The antimicrobial agent may be attached to the hydrogel via a variety of processes. As is shown in the experimental section the antimicrobial agent may be attached via immersion of the hydrogel in a solution comprising the antimicrobial agent. An antimicrobial agent may be applied substantially to the surface of the hydrogel via a surface application process as opposed to immersion. A solution comprising the antimicrobial agent may be dropped on to the surface of the hydrogel. A solution comprising the antimicrobial agent may be sprayed on to the hydrogel. As is shown in the experimental section the amount of antimicrobial agent required for antimicrobial activation of the surface is generally reduced significantly via dropping and spraying compared to immersion. This is because the bulk of the hydrogel is not activated with an antimicrobial agent.

In addition to the antimicrobial agent the hydrogel may comprise at least one therapeutic agent. Due to the ordered and repeating hydrophilic and hydrophobic domains of the hydrogel the therapeutic agent may be hydrophobic, hydrophilic, or amphiphilic, polar or non-polar. The antimicrobial hydrogel can host hydrophobic therapeutic agent(s) in the hydrophobic domain while the hydrophilic domains will host hydrophilic therapeutic agent(s). A therapeutic agent can be, but not limited to, drug molecules or small biomolecules such as peptides or proteins with anti-inflammatory, antibiotic or anticancer properties. This property of selective release of therapeutic agents from the antimicrobial hydrogels can, in addition to its antimicrobial properties, be used in medical devices such as for wound care and wound healing or other antimicrobial/drug release applications. At least one therapeutic agent may be covalently attached or physically absorbed to the hydrophobic and/or hydrophilic domains of the antimicrobial hydrogel. A plurality of therapeutic agents may be provided to the hydrogel. In such cases a first therapeutic agent may be covalently attached to the hydrogel and a second, third, etc. therapeutic agent may be physically absorbed. As opposed to the antimicrobial agent, the at least one therapeutic agent need not be immobilized on or within the hydrogel but may be free to substantially leach from the surface.

The antimicrobial hydrogel does not adhere or stick to biological surfaces like skin or a wound bed. This leads to improved performance in a variety of applications. A wound care article such as a wound dressing must be soft and be able to absorb the excess wound exudate in order to contain infection and keep the wound environment from harbouring microbes. The antimicrobial hydrogel can be used as a wound dressing to absorb uncontrollable exudates released from a compromised skin. Wound exudates can contain pus, blood, water, and sweat. Due to the high and versatile absorption properties of the antimicrobial hydrogel, in combination with the antimicrobial properties it is especially suitable as a wound care article. Table 2 in the experimental section shows that the antimicrobial hydrogel absorbs substantially the same amount of water compared to a hydrogel, comprising amphiphilic component, but without an antimicrobial agent covalently bonded thereto. The antimicrobial hydrogel therefore has sufficient wound exudate absorbing performance even when comprising an antimicrobial agent.

A device comprising the antimicrobial hydrogel may be formed by applying the antimicrobial hydrogel on a substrate. The substrate may have a greater mechanical strength than the hydrogel such that it is less susceptible to damage during use.

The term device used here refers to a medical, hygiene, or wound-care device where antimicrobial properties are advantageous. For example the device may be selected from the group comprising, personal hygiene articles, nappies, implants, surgical instruments, stents, catheters, skin grafts, contact lenses, wound dressings, ostomy dressings, ostomy baseplates, incision films, surgical drapes, patches, bandages, band-aids, plasters, adhesives, adhesive tapes, adhesive plasters, sticking-plasters, and court-plasters, and any combination thereof.

The device comprises a first layer being the antimicrobial hydrogel as described herein. The device may comprise a second layer, being the substrate referred to above, the second layer may comprise a hydrogel layer, such that the device comprises at least a first and second hydrogel layer. The second layer may comprise for example, a metal, a plastic, an elastomer, a film, a textile, a foam, a non-woven film, a fiber network, a knitted fabric. The second layer may be selected such that it has reduced liquid absorption properties compared to the first layer.

In the case of wound care or personal hygiene devices, where the device is to be applied on the skin of a patient, the first, antimicrobial hydrogel layer, is arranged to be proximal to the skin. The second layer, is thus arranged distal to the skin.

The second layer may be arranged on to the first antimicrobial hydrogel layer. A covering, adhesive or protecting layer may be arranged over the device.

As stated above, the antimicrobial hydrogel may be applied to an implant or implantable device such that the implant is provided with a non-leaching antimicrobial coating. Such implants may be screws, plates, shunts, artificial joints, artificial hearts, stents, catheters, airway tubes, conduits, valves etc. Similarly, the antimicrobial hydrogel may be applied to surgical instruments.

Figure 6:
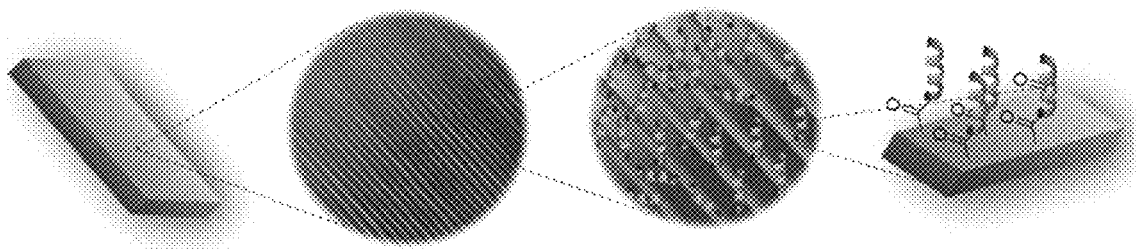
FIG. 6 shows a schematic of covalently bonded AMPs to a chemically cross-linked amphiphilic hydrogel with a repeating, 3D printed and aligned, normal hexagonal ordered nano structure.

The antimicrobial hydrogel may be formed into three dimensional structures via conventional casting techniques, or for example, additive manufacturing (AM) techniques. Additive manufacturing may improve the structure and orientation of the hydrophilic and hydrophilic domains. For example, during extrusion AM of the hydrogels, the shear and extensional forces orient the ordered nanostructure of the hydrogels in a preferred direction. Since the antimicrobial agents are attached to the hydrogel, this orientation or alignment of the hydrogel nanostructure can uniformly present the antimicrobial agents on the antimicrobial hydrogel in any preferred direction as shown in FIG. 6. This may lead to the antimicrobial agents uniformly to the external environment thus leading to improved attraction and killing of bacteria.

Although, the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

EXPERIMENTAL SECTION

The following examples are mere examples and should by no means be interpreted to limit the scope of the invention. Rather, the invention is limited only by the accompanying claims.

Experiment 1: Production of Antimicrobial Hydrogels

Formation of Cross-Linkable Amphiphilic Molecules
Summary

Amphiphilic tri-block co-polymers, polyethylene oxide (100)-polypropylene oxide(70)-polyethylene oxide(100) (Pluronic® F127), polyethylene oxide(30)-polypropylene oxide(70)-polyethylene oxide(30) (Pluronic® P123), chloroform, acryloyl chloride, triethylamine, sodium carbonate, anhydrous magnesium sulphate were all used as received. The diacrylate derivative of amphiphilic triblock co-polymers, Pluronic® F127 (DA-F127) (or) Pluronic® P123 (DA-P123) were synthesized by reacting the Pluronic molecule with acryloyl chloride (FIG. 1). All glassware was cleaned with acetone, ethanol and water, followed by drying at 100° C. in a convection oven, overnight.

Detailed Process

The reaction is performed in a three headed round bottomed flask (250 ml or 1 L) centre head for condenser, side heads; one for $N_2$ purging and one for adding Acryloyl Chloride dropwise.

18.9 g (0.0015 mol) of Pluronic F127 was weighed in a 500 ml beaker and to this 200 ml chloroform ($CHCl_3$) was added under magnetic stirring (400 rpm). The Pluronic F127 dissolved completely in $CHCl_3$ within 10 minutes. This solution was added to the round bottom flask. The beaker was washed with another 30 ml $CHCl_3$ to remove residual surfactant. The any residual surfactant and $CHCl_3$ was added to the round bottom flask.

Twice the molar amount of triethylamine, TEA, (0.303 g added as a solution with 10 ml $CHCl_3$) was added to the surfactant solution in the round bottom flask. TEA was added for neutralizing the hydrochloric acid (HCl) being produced during the reaction.

A solution of acryloyl chloride (0.006 mol, 0.5431 g) in chloroform (20 ml) was prepared. This solution was added to the round bottom flask dropwise using a dropper with elbow provision, (reaction vessel kept in cold water bath) under $N_2$ atmosphere ($N_2$ gas tube attached to glass pipette fitted to a rubber cork) with magnetic stirring at 400 rpm.

All junctions and openings were sealed with parafilm before leaving it overnight. The reaction mixture turned highly turbid after 3 hours (suggests neutralization of produced HCl by TEA). Depending on the increasing viscosity, added 20-30 ml of $CHCl_3$ to the reaction mixture intermittently. The reaction was stopped after 24 h and the reaction mixture was removed from the dropper side opening, emptied into the separating funnel.

The reaction products were washed 3 times with 100 ml aqueous $Na_2CO_3$ (5% by weight) in 250 ml or 500 ml separating funnel depending upon the amount of product. The two-phase mixture was agitated vigorously before allowing it to separate. A thick slow separating emulsion was formed. On the second or third wash, the separating funnel with mixture was allowed to stand overnight for a clear and complete separation. For each wash, the $CHCl_3$ phase was removed via the bottom release. The aqueous phase was removed from the top to avoid contamination.

The organic phase was transferred to a 500 ml beaker. Anhydrous magnesium sulphate (5 spatulas~20-30 g $Mg_2SO_4$) was added portion wise to the mixture and it was allowed to stand on magnetic stirring (200-300 rpm, RT) for 2 hours until a clear layer of $CHCl_3$ phase was formed.

A Buchner funnel was used for vacuum filtering off the $CHCl_3$ mixture into a conical flask. Prior to filtration, added a further 100 ml of $CHCl_3$ to the beaker containing the mixture, for dilution, which reduces the viscosity of mixture and helps prevent clogging of funnel channels. A 11 cm diameter Whatman filter paper was placed on the funnel channel openings for filtration. During the filtration, the filter paper was scraped in order to facilitate filtering process. The paper was changed when the filtrate production begins to slow down greatly. A water based vacuum system was used for filtration. The filtered clear solution was transferred to a previously weighed 1 L, 1 headed round bottom flask for solvent evaporation under reduced pressure.

The solvent was removed at reduced pressure at 40° C. for 2.5-6 hours. Most of the solvent was removed in the first 30 minutes and collected in both primary and secondary collection vessels. Following this, the evaporation was run at minimum possible pressure until a dry powdery residue was formed. This process takes almost 6 hours to reach completion. A white powdery residue was obtained at the end of evaporation.

An overall yield of 75-85% (DA-F127) was achieved. The above procedure was repeated to synthesize DA-P123.

Formation of Chemically Cross-Linkable Lyotropic Liquid Crystals Using the Cross-Linkable Amphiphilic Block-Copolymers For the present example, a micellar cubic LLC phase was formed using diacrylate modified Pluronic F127 (DA-F127) and water. The compositions by weight for this particular example are 30% DA-F127 and 70% water. This is followed by addition of photoinitiator 2-methyl 2-hydroxy propiophenone. The concentration of photoinitiator added was 1% by weight, of the total DA-F127 block co-polymer composition. To form a LLC gel, the diacrylate modified amphiphilic block copolymer, water and photoinitiator are mixed thoroughly in a glass container to form a viscous, clear, transparent gel. The container with the gel was then kept tightly sealed in a dark environment for 24 hours. The same procedure applies to all possible LLC phases that can be formed using the DA-F127 or DA-P123 amphiphilic block copolymers.

Formation of Three Dimensional, Solid and Chemically Cross-Linked Lyotropic Liquid Crystal Matrices According to the Invention The cross-linkable LLC gel was then either, transferred into a mould of preferred shape or additive manufactured (3D printed) using an extrusion additive manufacturing system to obtain the final shape of interest. This step was followed by crosslinking the shape-formed gel using ultraviolet-light (90W lamp, 252 nm) for 5-30 minutes to form a three dimensional, solid and cross-linked lyotropic liquid crystal hydrogel possessing alternating hydrophilic and hydrophobic nanostructure.

Formation of Chemically Cross-Linked Lyotropic Liquid Crystal Hydrogels, with Covalently Attached, Positively Charged Antimicrobial Peptides A solution of antimicrobial peptide RRPRPRPRPWWWW-NH2 (RRP9W4N, Red Glead Discovery AB, Lund, Sweden) was prepared in sterilized water to a concentration of 200 µM. For covalent attachment of the AMP to hydrogels, the hydrogels were submerged into a solution of 1-ethyl-3-(3-dimethylaminopropyl) carbodiimide hydrochloride (EDC) and N-Hydroxysuccinimide (NHS) in MES buffer (pH=6) at a final concentration of 2 mg/ml and were allowed to react for 30 min on slow shake at room temperature. The hydrogels were then washed 3 times in phosphate buffered saline (PBS, pH 7.4) and suspended in the AMP solution for 2 h in room temperature. The hydrogels were washed 3 times for 0.5 h to remove unreacted peptides from the material and used for bacterial assays.

TABLE 1

Compositions and details of antimicrobial hydrogels produced via the above process

| Type of Hydrogel | Amphiphilic Molecule | Ordered Nano-structure | AMP attached to Hydrogel | % wt. of Amphiphilic Molecule | % wt. of Water |
|---|---|---|---|---|---|
| DA-F127 Antimicrobial Hydrogel | DA-F127 | Normal micellar cubic | RRP9W4N | 30 | 70 |
| DA-F127 Antimicrobial Hydrogel | DA-F127 | Normal hexagonal | RRP9W4N | 70 | 30 |
| DA-P123 Antimicrobial Hydrogel | DA-P123 | Normal hexagonal | RRP9W4N | 45 | 55 |

Experiment 2: Testing Antimicrobial Activity and Non-Leaching of the Antimicrobial Hydrogels Testing immobilization and non-leaching performance of hydrogels Fluorescent tagged AMP (5(6) carboxyfluorescein-RRPRPRPRPWWWW-NH$_2$) was used to study the stability of AMP attachment and its distribution on hydrogel surfaces after multiple washing steps in ethanol for up to 3 weeks. To test the attachment efficiency of the AMP to the hydrogel, the antimicrobial hydrogel was washed sequentially in 50% ethanol for 3 weeks. After each wash at specific time points, the antimicrobial hydrogels were removed, tapped with tissue paper to remove excess solvent and was imaged under fluorescent microscope to assess the fluorescence emitted by the AMP. The results were compared with a control hydrogel, where fluorescent tagged AMP was absorbed in to the hydrogel by immersion, however, no covalent bonding of the tagged AMP occurred. FIG. 3a (upper row) shows that the fluorescence emitted by the AMP covalently bonded to the hydrogel remains intact at different time points after washing. FIG. 3b (lower row) shows the control. As can be seen in the figure, immobilization was significantly greater with the covalently bonded AMP.

Evaluating Anti-Microbial Activity of the Antimicrobial Hydrogel

*S. epidermidis* (ATCC 35984), were used to assess biofilm formation on the antimicrobial hydrogels. One day before the experiment a sterilized 10 µL loop was used to withdraw a single colony from cultured agar plates of each bacterium to inoculate a tube of 5 mL tryptic soy broth (TSB). The inoculated cells were cultured in an incubator for 6 h, diluted in TSB and cultured in the incubator overnight to reach the stationary phase for bacterial growth.

Figure 4B:
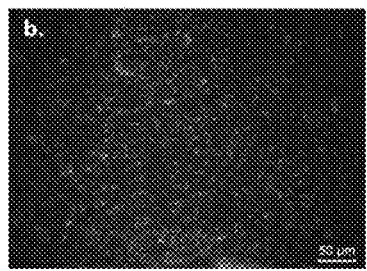
Figure 4C:
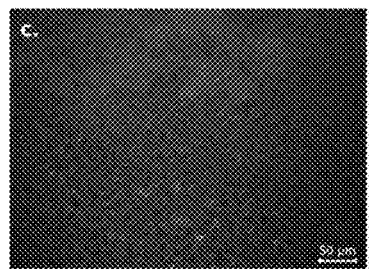

The optical density of the bacteria culture was adjusted to 0.7 at 620 nm (estimated to give $10^9$ colonies) using a spectrometer. The bacterial suspension was centrifuged for 10 minutes at 2500 rpm and the formed bacteria pellet was suspended in the fresh TSB media. 2 mL of the suspension was seeded onto the negative-control glass substrates, negative control hydrogels, positive-control hydrogels, and amphiphilic antimicrobial hydrogels according to an aspect of the invention, in a 12 well plate. The negative control hydrogels had the ordered and repeating structure described above but were not provided with any antimicrobial agents (AMPs). The positive control hydrogels had AMPs absorbed in to the hydrogel but no covalent bonding of the AMP to the hydrogel occurred. Bacteria were then cultured for 24 hours under standard culture condition (ambient air at 37° C.) to promote biofilm formation onto the surfaces. After 1 hour of culture, the media was aspirated and replaced with fresh TSB for another 23 hours culture. At the end of 24 h time point, the control and antimicrobial hydrogel samples were rinsed 3 times with fresh PBS to wash off any unattached planktonic bacteria before biofilm analysis. The biofilm was stained using LIVE/DEAD® BacLight™ Bacterial Viability Kit (Molecular probes, Invitrogen). The images in FIG. 4 were obtained with SYTO® 9 and propidium iodide nucleic acid staining provided in the kit. Live bacteria with intact cell membranes appeared green and dead bacteria with compromised membranes appeared red. FIG. 4a shows *S. epidermidis* biofilms formed onto the negative control hydrogels without any AMP. FIG. 4b shows *S. epidermidis* biofilms formed onto positive control hydrogels with physically absorbed AMPs, that is, not covalently bonded. FIG. 4c shows *S. epidermidis* biofilms formed on to hydrogels with covalently bonded AMPs according to an aspect of the invention. FIG. 4b shows that there is less bacterial attachment on the positive hydrogel control. Whilst FIG. 4c shows almost 100% antimicrobial effect, that is, bacterial killing on the antimicrobial hydrogels.

Experiment 3: Evaluating Liquid Absorption Capacity of the Hydrogel and Antimicrobial Hydrogel The DA-F127 and DA-P123 based hydrogels and antimicrobial hydrogels with normal micellar cubic and normal hexagonal ordered nanostructure was used for the liquid absorption studies. Small pieces of hydrogels were freeze dried for 2 days to remove all water present in the hydrogels. For those hydrogels in fully-wet state, testing was done without any additional drying step. After drying, the hydrogels was in dry state and was placed in excess water or chloroform (20 ml) overnight to let the hydrogels absorb as much liquid as possible. Following absorption for 15 hours at ambient temperature, the hydrogels were removed from the respective liquids using tweezers and excess liquids were removed by tapping onto a tissue paper. Following this the samples were weighed to 0.001 g accuracy. Table 2 shows the initial, final and liquid absorption capacity (LQ %) of each hydrogel in both water and chloroform. The antimicrobial hydrogels were only tested in water since water was more relevant for the study. The following equation was used to calculate the liquid absorbance of the hydrogels and antimicrobial hydrogels, $$\text{Liquid absorbency } (LQ) \% = \frac{\text{Final weight} - \text{Initial weight}}{\text{Initial weight}} * 100$$

TABLE 2

Liquid absorption of the fully dry hydrogels and antimicrobial hydrogels-micellar cubic ordered nanostructure

| Type of Hydrogel | Amphiphilic molecule | % wt. Amphiphilic molecule | % wt. water | Liquid Absorption in Water | | | Liquid Absorption in Chloroform | | |
|---|---|---|---|---|---|---|---|---|---|
| | | | | Initial Weight (g) | Final Weight (g) | LQ % | Initial Weight (g) | Final Weight (g) | LQ % |
| Hydrogel | DA-F127 | >95 | <5 | 0.142 | 1.187 | 750.0 | 0.185 | 3.410 | 1794.4 |
| Antimicrobial Hydrogel | DA-F127 | >95 | <5 | 0.148 | 1.149 | 676.4 | — | — | — |

Zone Inhibition Test

Figure 5A:
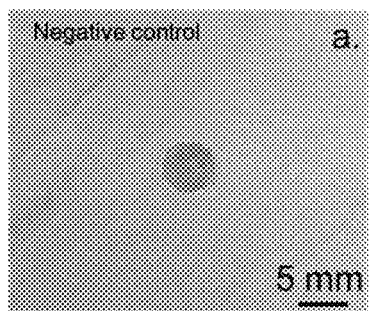
FIG. 5*a* shows a negative control amphiphilic hydrogel with no AMPs.
Figure 5B:
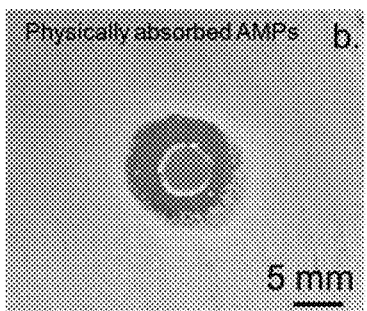
FIG. 5b shows an amphiphilic hydrogel with only physically absorbed AMPs.
Figure 5C:
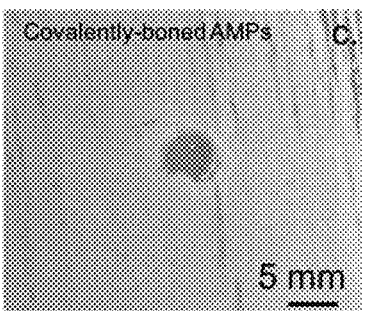
FIG. 5c shows amphiphilic antimicrobial hydrogel according to an aspect where AMPs are covalently attached to the amphiphilic hydrogel.

One day before the experiment, a sterilized 10 μHoop was used to withdraw a single *S. aureus* colony from cultured agar plates to inoculate a tube of 5 ml tryptic soy broth (TSB). The inoculated cells were cultured in the incubator for 6 h, diluted in TSB and incubated to reach the stationary phase for bacterial growth. 50 μl of the suspension was seeded onto brain heart infusion (BHI) agar plates, followed by placing the hydrogels on the agar. Plates were then incubated under standard culture conditions (ambient air 37° C.) for 24 hours. In FIG. 5b, the clear region appeared around the hydrogels with physically absorbed AMPs is an indication of effective inhibition of microbial growth due to diffusion of AMPs from the gels. On the other hand, as shown in FIG. 5c, when the AMPs are attached covalently to the hydrogel, no clear region is observed around the hydrogels and the inhibition is only observed at the region directly below the hydrogel-covered area, meaning that no AMP leached out from the gel.

Table 2 shows that the dry state hydrogels have a liquid absorbency of up to 1795% in chloroform while it can absorb 750% of water. Importantly, antimicrobial function of the hydrogels does not drastically change the liquid absorbency of the hydrogels with water absorbency at 676% for the antimicrobial hydrogels.

TABLE 3

Liquid absorption of various hydrogels according to the invention in fully wet-state

| Type of Hydrogel | Amphiphilic molecule | % wt. Amphiphilic molecule | % wt. water | Liquid Absorption in Water | | |
|---|---|---|---|---|---|---|
| | | | | Initial Weight (g) | Final Weight (g) | LQ % |
| Hydrogel-Normal Cubic Micellar-Ordered | DA-F127 | 30 | 70 | 0.006 | 0.017 | 183.3 |

TABLE 3-continued

Liquid absorption of various hydrogels according to the invention in fully wet-state

| Type of Hydrogel | Amphiphilic molecule | % wt. Amphiphilic molecule | % wt. water | Initial Weight (g) | Final Weight (g) | LQ % |
|---|---|---|---|---|---|---|
| Hydrogel-Normal Hexagonal-Ordered | DA-F127 | 70 | 30 | 0.008 | 0.033 | 312.5 |
| Hydrogel-Normal Hexagonal-Ordered | DA-P123 | 45 | 55 | 0.006 | 0.007 | 16.67 |

Fully wet state in Table 3 refers to the original concentration of the hydrogel of 20-80% water and 20-80% amphiphilic organic molecules by weight. The high liquid absorbance makes the hydrogels particularly suited for use in wound dressings where liquid absorbance of wound exudate is important.

Conclusions

An amphiphilic antimicrobial hydrogel has been prepared which displays improved properties compared to existing hydrogels. Covalent bonding of antimicrobial agents to the hydrophilic domains and/or hydrophobic domains of the amphiphilic hydrogel results in immobilization of antimicrobial agents to the hydrogel. Furthermore, the amphiphilic antimicrobial hydrogel is capable of absorbing both aqueous and non-aqueous hydrophobic solutions to a significant extent.

Experiment 4: Formation of LLC Hydrogels, Covalent Attachment of AMPs and Subsequent Characterization and Analysis Synthesis of Diacrylate Modified Pluronic F-127

The Pluronic F127 in its original form is not capable of being chemically cross-linked. Instead it is a solution of ever-changing LLCs responding to different concentration and temperature. Here a solid hydrogel was desired, which meant that the Pluronic had to be modified in order for it to be chemically (or covalently) cross-linkable. This was done by adding acrylate groups at the ends of the amphiphilic polymer, which has been proven to be successful in earlier studies (He, W. et al Mesoscopically Ordered Bone-Mimetic Nanocomposites. Adv. Mater., Vol 27: 2260-2264) and as described above. A general schematic of the chemical reaction is shown in FIG. 1. A detailed description of the synthesis process can be found in He, W. et al, 2015.

Formation of Amphiphilic Hydrogels

The diacrylate derivative of Pluronic F127 is essentially a white powder similar in appearance to its parent molecule. The powder was mixed with water to form a desired LLC. This study only utilized the micellar cubic phase (denoted in shorthand as Ii) since the Ii phase is easier to form and handle and only requires low amounts of the amphiphile when compared to other LLC structures such as the hexagonal or lamellar phase, which is much thicker and requires a larger concentration of the amphiphile. LLCs in the micellar cubic phase were obtained by manually mixing the diacrylated Pluronic F-127 (DA-F127) (40 wt %) with water (60 wt %), to form a thick and homogenous gel. A photoinitiator, 2-hydroxy-2-methylpropiophenone was added to the gel mixture corresponding to 2 wt % of the DA-F127 in order to facilitate crosslinking. Another, non-cytotoxic photoinitiator called 2-Hydroxy-4-(2-hydroxyethoxy)-2-methylpropiophenone was also used for parts of this study. The gel mixture was then spread between two glass slides to get an appropriate thickness, which was then wrapped in Parafilm and aluminium foil. The gel was kept undisturbed overnight, in order for the LLC phase to reach its equilibrium state. The following day, the gel, still in between the glass slides, was exposed to UV-light ($\lambda$=254 nm) for 10 minutes to cross-link the gel. A solid hydrogel was obtained and cut into the desired shape with the help of circular biopsy punches that had the diameters of 4 mm (subsequently referred to as small hydrogels) and 8 mm (subsequently referred to as big hydrogels). For the hydrogels with greater diameter, a plastic mould was used with a thickness of 1.8 mm to also get a uniform thickness. The last step was to wash the hydrogels in water for 48 hours in order to remove the initiator and the non cross-linked polymers as well as to get the hydrogels into their fully swollen state.

Covalent Attachment of AMPs to the Amphiphilic Hydrogels

The different types are referred to as control hydrogels without AMP, hydrogels with physically loaded AMPs and hydrogels with covalently attached AMPs. The control hydrogel was used in all experiments and consisted only of the cross-linked hydrogel. The second variant, physically loaded AMPs, are hydrogels that were soaked in the 200 µM AMP solution for 2 hours. Essentially, the second variant does not induce any covalent linkage between the AMP and the hydrogel. The last variant called the covalently attached AMP samples, were obtained as follows: following the washing step of the previous section, the hydrogels were put in separate wells of a 24 well plate. N-hydroxysuccinimide (NHS) and 1-Ethyl-3-(3-dimethylaminopropyl) carbodiimide (EDC) were weighed individually in order to make a 2 mg/ml solution in 2-(N-morpholino) ethanesulfonic acid (MES) buffer (with a pH of 6.00). 500 µl each of the EDC and NHS solutions were added to each well rapidly after the solutions were made since they have a short half-life. The hydrogels were left in the EDC/NHS solution for 30 minutes, followed by washing in water. After the EDC/NHS activation, the hydrogels were soaked in the AMP solution for 2 hours. The concentration and the volume of the solution varied depending on the experiment. Unless otherwise mentioned, the concentration and volumes used throughout all experiments was 200 µM and 400 µl for the small hydrogels and 700 µl for the big hydrogels. described above in Experiment 1 and shown in the reaction scheme presented in FIG. 2.

Fourier Transform Infrared Spectroscopy (FITR) Analysis

The reaction shown in FIG. 2 can only occur when there is a carboxylic acid present on the Pluronic molecule. However, the DA-F127 only contains an ester group and not a carboxylic acid group. So, in order for the reaction to happen, somewhere during the formation process of the hydrogel, prior to the EDC/NHS activation, carboxylic acid groups must have been formed. In an attempt to investigate this reaction, FTIR measurements were done on samples from all the different steps prior to the AMP attachment step. This included non-modified Pluronic F127 powder, DA modified Pluronic F127 powder, cross-linked hydrogels (washed and un-washed), and finally EDC/NHS activated hydrogels. The FTIR analysis was performed on a Perkin Elmer Frontier spectrometer using the attenuated total reflectance mode (ATR, GladiATR diamond plate from Pike Technologies). The scan range was over a wavenumber of 400-4000 cm$^{-1}$. The samples were 1-2 mm thick and each sample was scanned 16 times.

The spectra in the range of 1500-1900 cm$^{-1}$ of the five different samples are shown in FIG. 10. The non-modified Pluronic F127 in powder form did not show a distinct peak in this region. The modified Pluronic powder on the other hand showed a distinct peak at 1725 cm$^{-1}$. The cross-linked hydrogel, cross-linked & washed hydrogel and EDC & NHS activated hydrogel, all showed distinct peaks at 1734, 1734 and 1735 cm$^{-1}$ respectively.

On the non-modified Pluronic F127, there is no clear separate signal in the ketone region, indicating the absence of carbonyl in this molecule. A clear signal is on the other hand found in the FTIR measurements of the modified Pluronic F127, indicating a successful incorporation of the acrylate-groups. The only difference in between steps where a signal is observed is between the modified Pluronic F127 and the cross-linked hydrogel, which show a peak shift from 1725 cm$^{-1}$ to 1734 cm$^{-1}$. This peak most likely indicates that the reaction has a yield of less than 100% and there is therefore a mix of normal esters, conjugated esters and carboxylic acids throughout the hydrogel.

Peptide Concentration Measurements with UV-Visible (UV-Vis) Spectroscopy

UV-Vis spectrophotometry was applied to estimate the amount of AMP present within the hydrogel. The hydrogels were first activated in the standard fashion as described above and after they were exposed to the AMP solution, all the liquid was gathered and transferred into vials into which water was added, to a total volume of 3 ml. This diluted solution was transferred into a quartz cuvette, which was placed inside an HP8453 spectrophotometer. Measurements were performed with water as the reference and the absorbance at 280 nm were noted down. This wavelength correlates to the absorption region of the amino acid tryptophan. An external standard of the peptides was made prior to measurements in order to correlate the measured wavelengths to a corresponding concentration. Analyses were done on both big (8 mm diameter) and small (4 mm) hydrogels as well as on both covalently attached AMP-hydrogels and physically loaded AMP-hydrogels. The hydrogels were re-washed after they were soaked in the AMP solution and measurements were performed on the washed extract to quantify the leaching of AMPs out from the hydrogels.

Results showing the amount of attached, or absorbed in the case of the physically loaded AMP-hydrogels are shown in Table 4.

TABLE 4

The amount of attached or absorbed AMP in the hydrogel, presented in mg ± standard deviation.

| Sample | Attached/absorbed AMP (mg) |
| --- | --- |
| 4 mm, covalently attached AMP | 0.031 ± 0.013 |
| 4 mm, physically absorbed AMP | 0.035 ± 0.015 |
| 8 mm, covalently attached AMP | 0.091 ± 0.025 |
| 8 mm, physically absorbed AMP | 0.093 ± 0.028 |

Table 4 indicates that hydrogels physically loaded with AMPs and hydrogels to which AMPs are covalently attached take up a similar amount of AMP. This indicates that amphiphilic LLC hydrogels, mostly likely due to the mechanism of the hydrophobic effect, efficiently incorporate AMPs even if only physically absorbed.

Qualitative and Quantitative Evaluation of Biofilm Formation and Antibacterial Activity of Amphiphilic Hydrogels In this experiment the antimicrobial effect of the hydrogels was tested according to the protocol in experiment 2, however, it was repeated with three separate bacterial strains: Staphylococcus aureus CCUG 10778, Staphylococcus epidermidis ATCC 35984 and Pseudomonas aeruginosa CCUG 6489. These bacteria were chosen since they are commonly found in infections, and because the Pseudomonas genus is gram negative while the Staphylococci genus is gram positive. All bacteria were stored in a freezer at −80° C. and were only taken out briefly in order to form colonies for cultivation. This was done on Brain-Heart Infusion agar plates (BHI agar plates) which were streaked with sterile technique and then incubated upside down in a 37° C. incubator overnight. A selection of microscopy images taken of the bacteria present on the hydrogel samples after the LIVE/DEAD staining are presented in FIG. 7. Generally, S. aureus and S. epidermidis were fully viable on the control hydrogels forming a biofilm structure over the major part of the sample. P. aeruginosa, did not seem to grow as efficiently as the gram positive Staph species. In several occasions there were few, if not no bacteria on the hydrogels cultured with P. aeruginosa. The results have been analysed with regard to the proportion of dead cells found on the surface using the formula, (dead cells)÷(dead+alive cells). The quantative results are shown in FIG. 8.

Figure 7A:
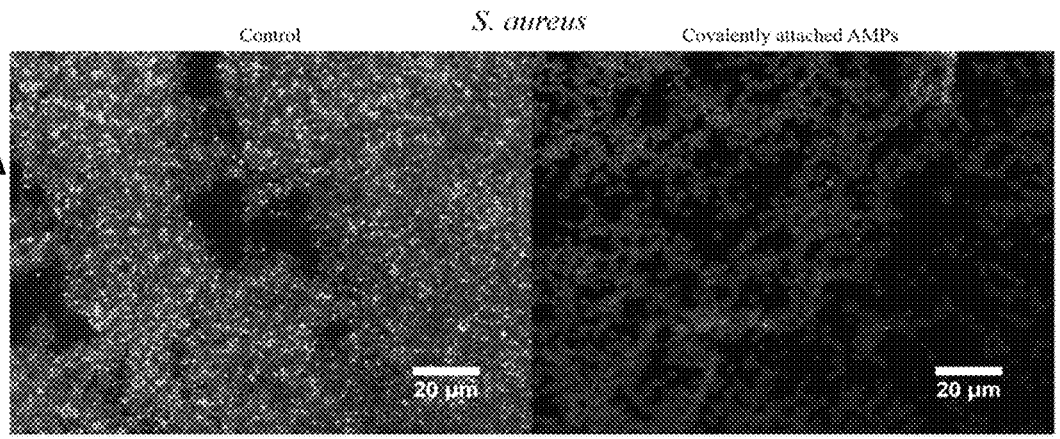
FIG. 7a shows S. epidermis.
Figure 7B:
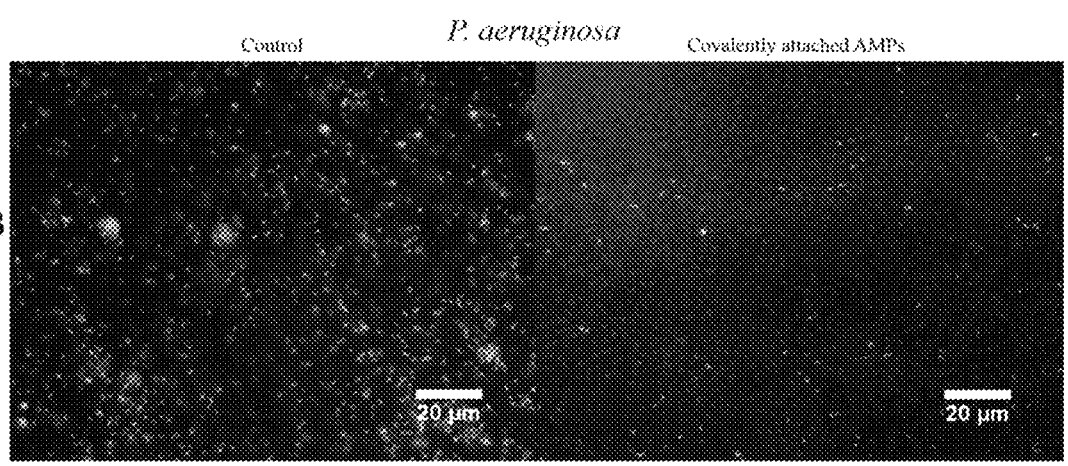
FIG. 7b shows images of P. aeruginosa.
Figure 7C:
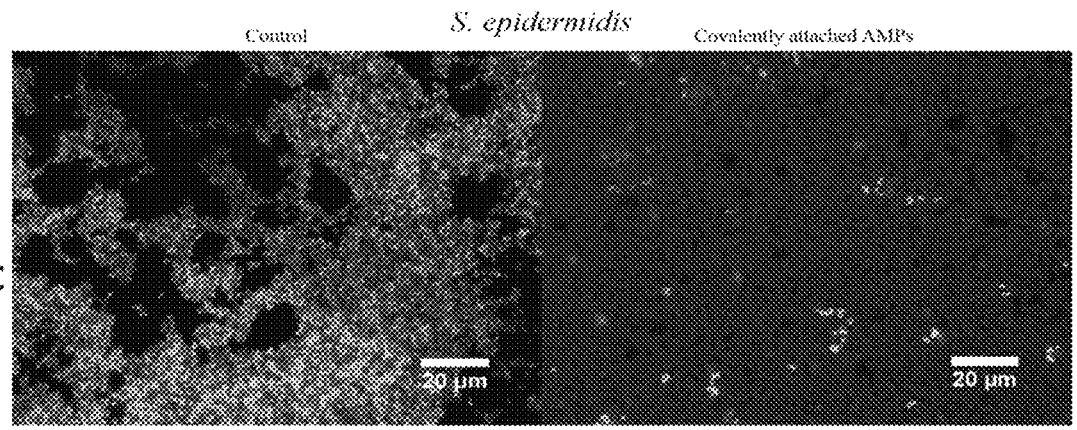
FIG. 7c shows S. aureus.
Figure 9A:
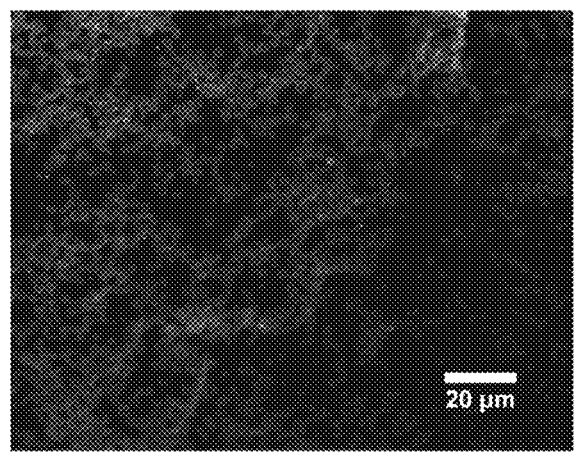
FIG. 9 shows live/dead fluorescent images of bacterial colonies/biofilms formed on the surface of an antimicrobial amphiphilic hydrogel according to an aspect. The dead cells display different morphologies in each of the three images.
Figure 9B:
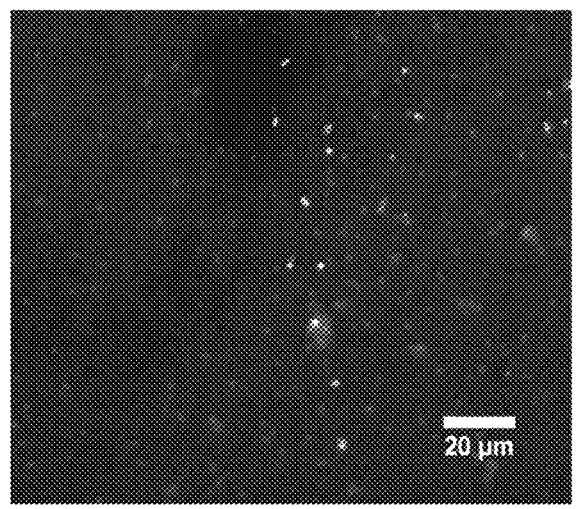
Figure 9C:
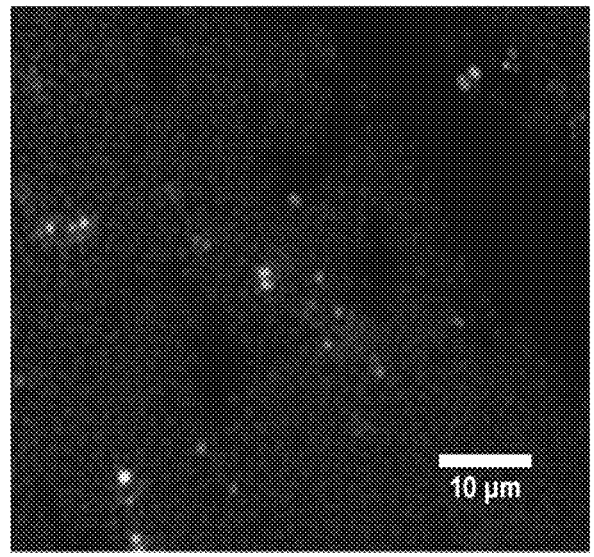
Figure 10C:
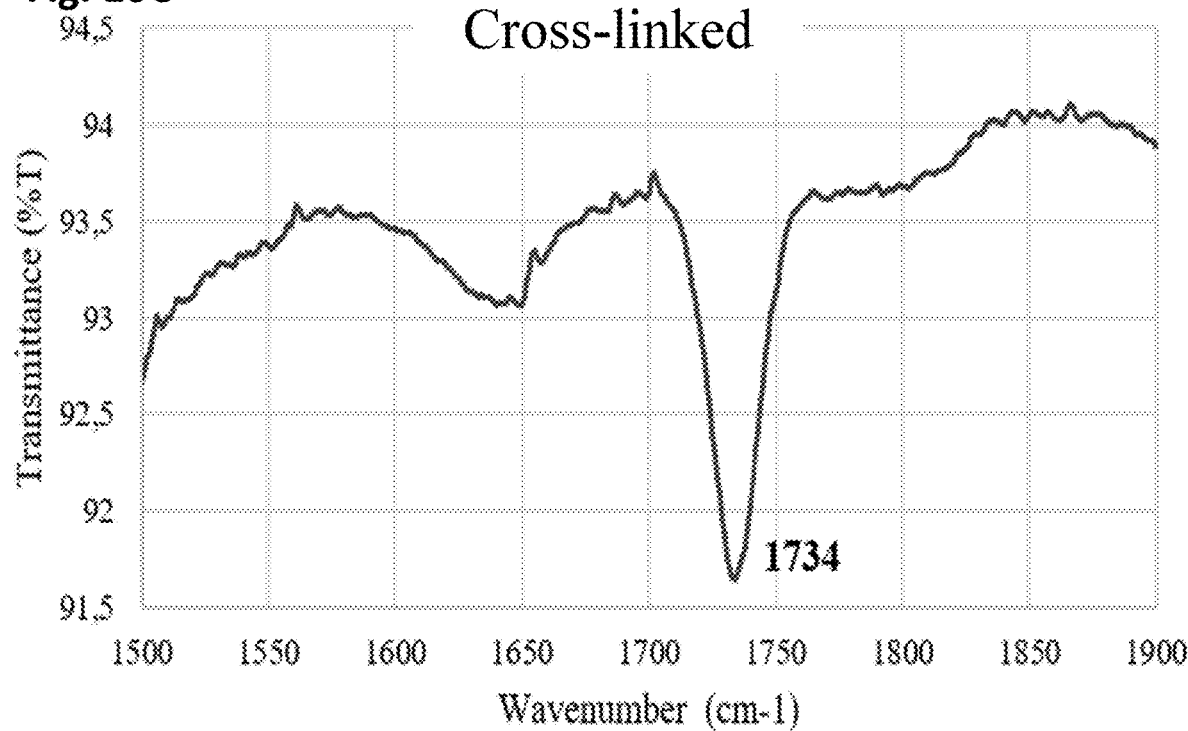
FIG. 10 shows The FTIR spectra between the wavenumber 1500 and 1900 $cm^{-1}$ of the five different samples: a) non modified, b) modified, c) cross-linked, d) cross-linked and washed and e) EDC & NHS activated. The wavenumbers ($cm^{-1}$) are found along the x-axis and the transmittance (% T) is found on the y-axis. A clear signal is found in all samples apart from the non-modified sample. Non-modified denotes a sample which contains the block-copolymer, however which cannot be crosslinked due to lack of acrylate functional groups.
Figure 10D:
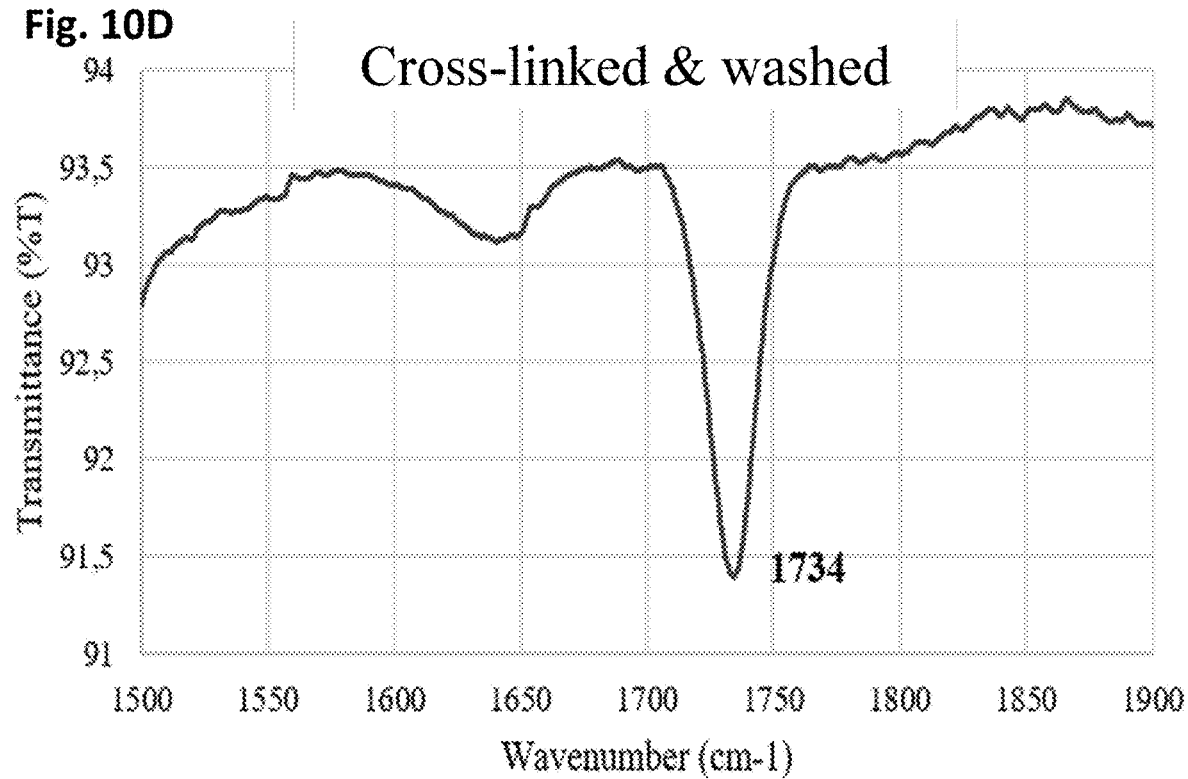
Figure 10E:
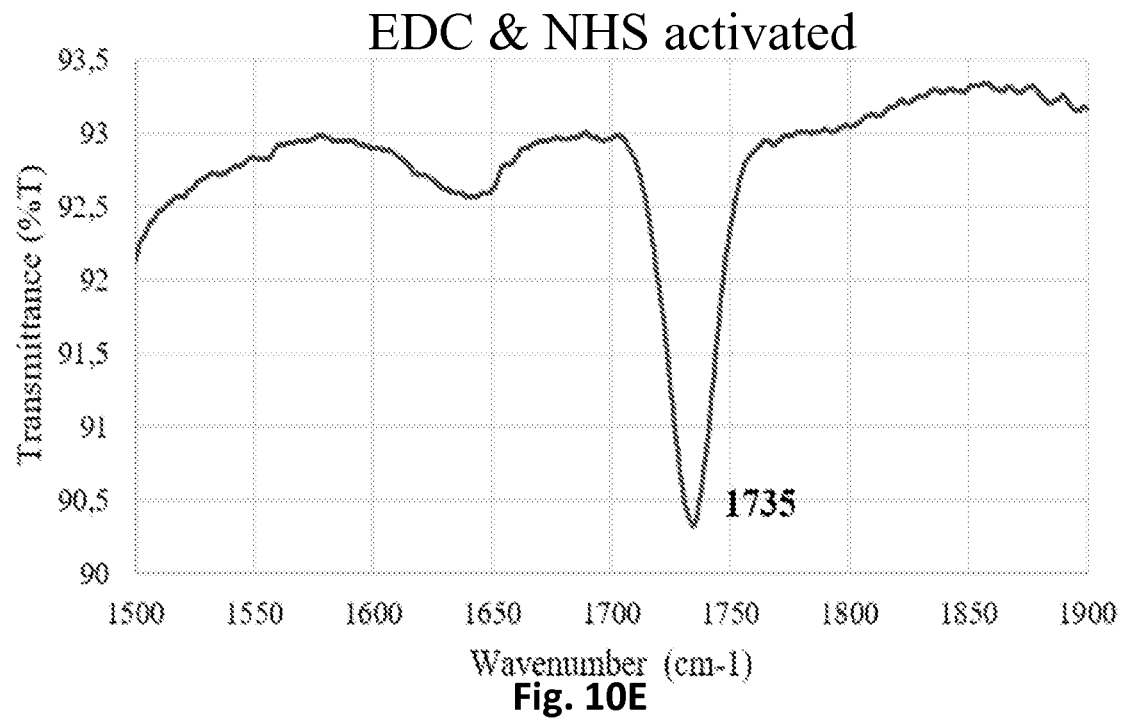

As is clear in both FIGS. 7 and 8, the incorporation of the AMPs to the material produces a major antibacterial effect on the bacteria that are in direct contact with the surface. Most of the bacteria were dead and the ones that were alive were relatively few when compared to the control and were, for most of the time, separated into small gatherings. Biofilm formation was therefore kept to a minimum, suggesting that the alive bacteria on the hydrogel surface might be more easily taken care of by the body's own immune response. If sterility is of utmost importance, conventional antibiotics could be used together with the AMP-hydrogel, which should result in fewer bacteria that survive the treatment and hence consequentially lower antibiotic resistance in these cases. FIG. 9 shows the different morphologies of dead cells. Both the irregular blobs shown in FIG. 9a, and the powder-like structure of FIG. 9b imply a compromised structural integrity of the bacterial membrane. This would mean that even though the peptides are far too short to fully penetrate the membrane, they still exert their activity by interfering with the membrane most likely via the electrostatic forces.

Storage Stability in PBS

Figure 11A:
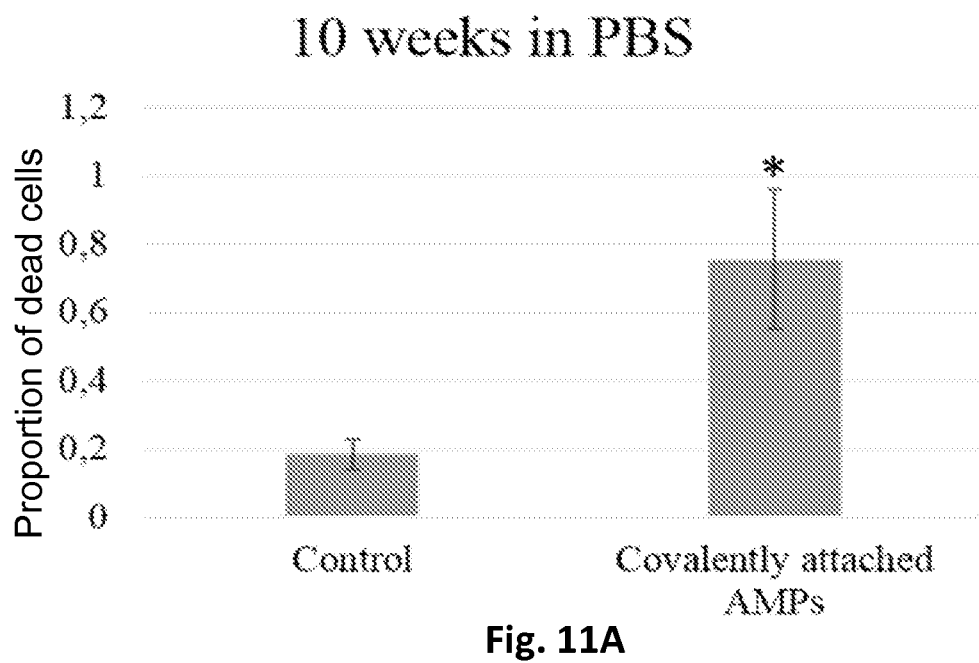
In FIG. 11a the proportion of dead cells (S. aureus) can be viewed for a control amphiphilic hydrogel and an antimicrobial amphiphilic hydrogel.
Figure 11B:
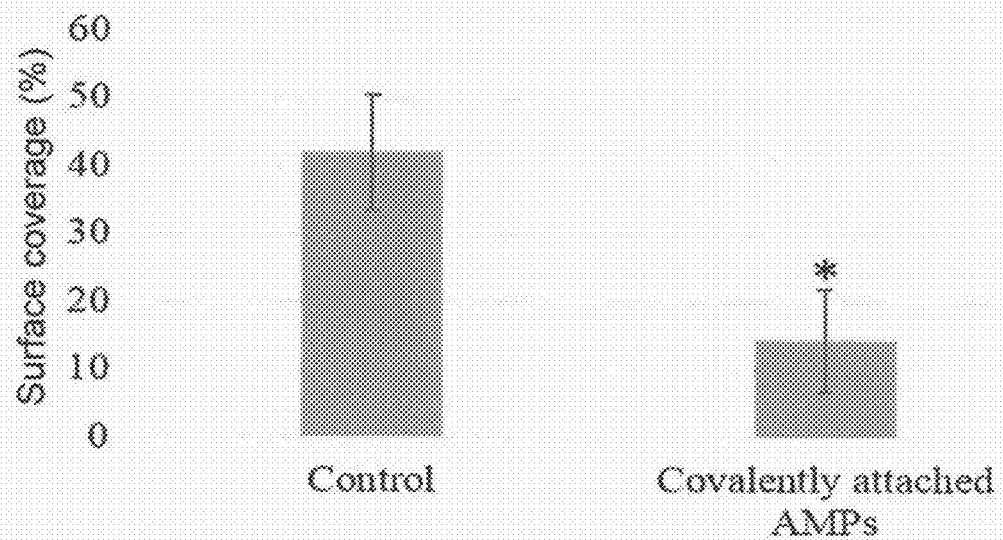
FIG. 11b shows the total surface coverage found on the hydrogels. The astreix (*) indicates a significant difference compared to the control sample at a 95% confidence level.

To determine the stability of the amphiphilic hydrogels a storage stability experiment was performed. Big hydrogels were left for 10 weeks in PBS and then incubated with S. aureus and again followed by LIVE/DEAD staining as described above. Hydrogels that had been left in PBS for 10 weeks, with and without AMPs, were then incubated together with S. aureus. The results from the LIVE/DEAD staining of the bacteria are presented in FIG. 11. Both the proportion of dead cells, a), and the surface coverage of bacteria, b), are shown and a significant difference was found in both of them.

Serum Stability

Figure 12:
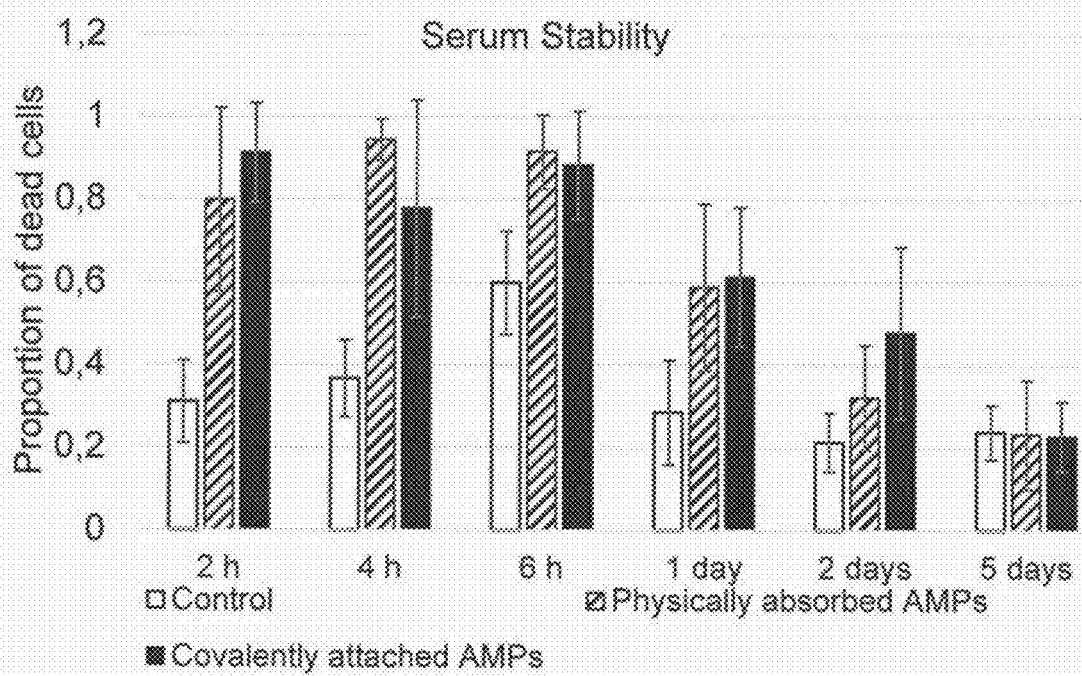
FIG. 12 shows the results from a serum stability test where the hydrogels were exposed to 20% human serum. The hydrogels were taken out from the serum at the times indicated on the x-axis. The proportion of dead cells (S. aureus) on the surface of the hydrogels were determined by live/dead staining and is found on the y-axis. At each time point, except at 5 days, there was a significant difference at a 95% confidence level between the activated surfaces compared to the control. Each bar is compiled of images taken of two samples.

To evaluate the stability of the covalent attachment of AMPs to the amphiphilic hydrogel, hydrogels were put in human serum. Big hydrogels according to the above procedure were made and were put in separate wells of a 24 well plate. To each well, 400 µl of 20% human serum was added after filtration through a 0.2 µm filter in order to remove bacteria and precipitates. The serum was bought from Sigma Aldrich as pure serum and was diluted to 20% with Milli-Q water. The plates were kept in room temperature, wrapped in aluminium foil. At the desired time points, a set of hydrogels (2× control, 2× physically and 2× covalently) were taken out from the serum and washed three times in PBS. The hydrogels were placed in a new 24 well plate where a culture of S. aureus was allowed to grow on them overnight in a 37° C. incubator. Following incubation, the hydrogels were stained with the LIVE/DEAD viability kit and the results were analysed. The results are presented in FIG. 12. The results show that during the first 10 hours, normal activity was achieved. Bactericidal effect was still observed on the covalently attached AMP-hydrogel samples even after 1 and 2 days in serum, which was significantly higher than the control.

Surface Application of AMPs to Hydrogels

Trials were done in order to minimize the amount of AMP used to activate the hydrogel without compromising the bactericidal effect. This was done in two different ways, either by adding drops of the AMP solution onto the hydrogels, or by using a spray device. For the drop test, four different volumes and two different concentrations were used, which resulted in eight different combinations. The different combinations are summarized in Table 5. As a comparison, the 400 µl of 200 µM solution that the small hydrogels were normally activated in via immersion contained 154.5 µg of the AMP molecule. The AMP was weighed carefully and then diluted in water to reach the desired concentration of 800 µM. A part of this solution was diluted to 200 µM for the lower concentration. The hydrogels were made in similar fashion as described in experiment 2 and were then activated in EDC/NHS as previously. After this, the hydrogels were quickly dabbed with a tissue to dry the surface. The drops were then distributed on top of the hydrogels with the help of a pipette according to Table 5. The drops were kept on the hydrogels for 3 hours and were followed by 3× washing in water. The antibacterial effect was evaluated against S. aureus grown in the same fashion as previously described in experiment 2 and were analysed with LIVE/DEAD staining.

TABLE 5

Different combinations used in the drop test.

| Volume | AMP concentration | Amount of AMP in drop |
|---|---|---|
| 10 µl | 200 µM | 3.83 µg |
| 20 µl | 200 µM | 7.65 µg |
| 40 µl | 200 µM | 15.30 µg |
| 90 µl | 200 µM | 34.434 µg |
| 10 µl | 800 µM | 15.30 µg |
| 20 µl | 800 µM | 30.61 µg |
| 40 µl | 800 µM | 61.22 µg |
| 90 µl | 800 µM | 137.74 µg |

Figure 13:
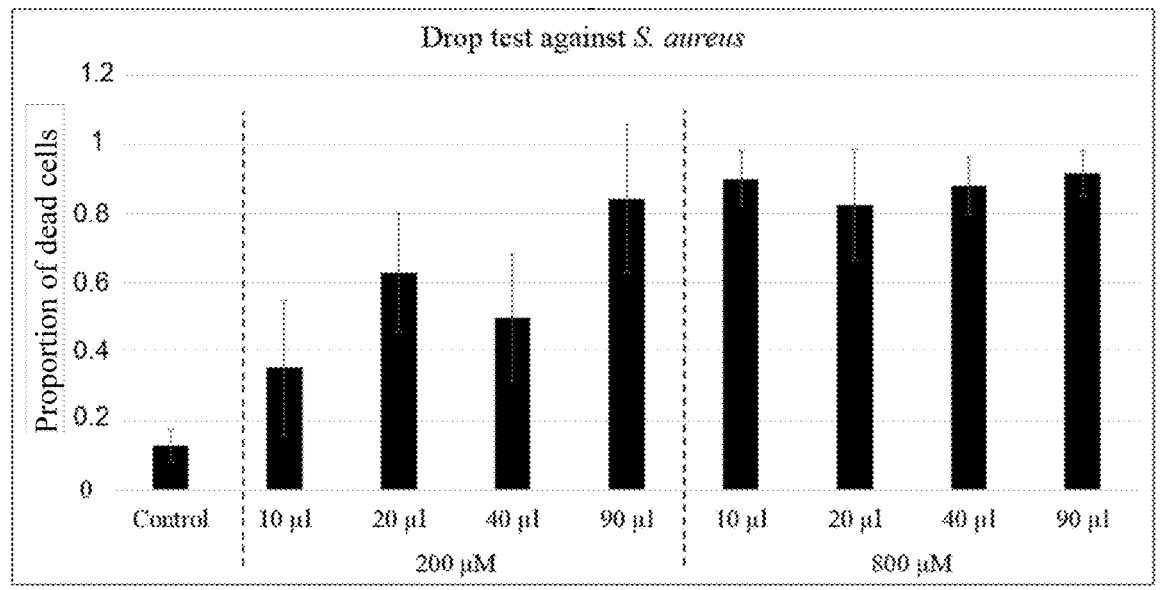
FIG. 13 shows the proportion of dead cells calculated from live/dead staining of hydrogel surface activated by the different drops containing AMP. All AMP activated samples showed a significant difference at a 95% conficence compared to the control.

Results are shown in FIG. 13. All samples showed a significant difference from the control. Hydrogels activated using drops of 200 µM AMP solution showed a relatively lower antibacterial effect compared to the immersion technique. The hydrogels activated by 800 µM drops showed the same antibacterial effect, all in the same region as the hydrogels that were activated in the soaking fashion mentioned above. It was observed that the larger volumes i.e. 40 µl and 90 µl did not always stay as a drop on the hydrogels but instead flowed away from the hydrogel. This may, for instance, explain the larger error bars for the 200 µM 90 µl samples and the apparent reduction in activity for the 200 µM 40 µl drops For the spray test, the hydrogels were activated with EDC/NHS before they were cut into the circular discs with the biopsy punch, and only one side was treated. Therefore, the whole sheets were activated rather than the small discs. This was done in order to get an even layer of sprayed substance upon the hydrogels and also to simulate how the hydrogels would most likely be activated in an industrial manner of production. The spray gun used in these studies was the A470 series from AZTEK® airbrush system. Two types of hydrogels were analysed, hydrogels that had been washed for 48 hours in water and hydrogels that were freshly crosslinked without any washing step prior to AMP activation. All these hydrogels were made with the non-cytotoxic photoinitiator in a further attempt to simulate an industrial approach. The AMP concentrations used in this experiment were 200 µM, 400 µM and 800 µM. The exact volume of liquid that was sprayed onto the surface is difficult to estimate due to losses during the spraying process. However, a rough estimate is that around 500 µl of the AMP solution was used per 10 cm$^2$ of hydrogel.

Figure 14:
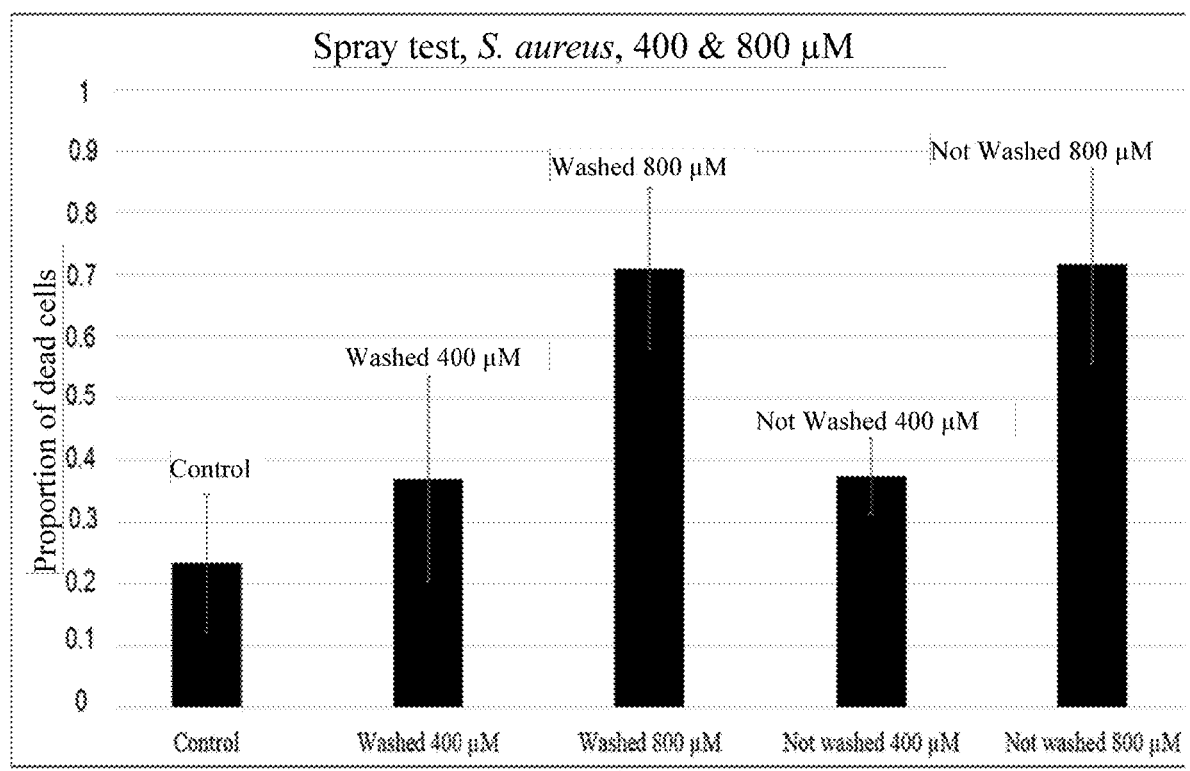
FIG. 14 shows the results of surface activation of hydrogels by spraying the AMP solution on the surface of the hydrogel. The surfaces were studied via live/dead staining of biofilms on the surface of hydrogels. The proportion of live/dead cells was calculated according to the aforementioned image analysis macro. All AMP activated samples showed a significant difference compared to the control sample at a 95% confident level.

In the first trial the sheets of hydrogels were activated with a 200 µM, 400 µM AMP, and 800 µM AMP solutions. Rectangular sheets of the hydrogel that had been washed for 2 days in water, and those that were fresh from the cross-linking were used. This means that hydrogels that were both fully swollen (approx. 90% water) and those that were in between the dry and fully swollen state (approx. 60% water). For both kinds of sheets, the hydrogels were not washed inbetween in order to remove any excess EDC/NHS and hence were left on the hydrogel when the AMP was added, as it was determined that this might lead to increased performance compared to washing off the EDC-NHS solution from the hydrogels prior to the application of the AMP solution. Results for the 400 µM and 800 µM AMP solutions are shown in FIG. 14. Spraying with a 200 µM AMP solution lead to reduced performance. As no significant difference was found if the hydrogels had been allowed to swell or not, these results indicate that it should be fully possible to activate the hydrogels directly after the cross-linking Human Cell Toxicity of the Amphiphilic Antimicrobial Hydrogel—MTT Assay To study the toxicity of the hydrogels to human cells, an MTT assay was performed on control hydrogels and hydrogels with covalently attached AMPs. An MTT assay measures the cell metabolic activity, which correlates to the viability of the cells. Hydrogels were made according to the above process and were cut into discs with a smaller biopsy punch measuring 4 mm in diameter. They were then washed for 48 hours in water followed by 30 minutes in ethanol and then again in Milli-Q water. One half of the hydrogels were activated, followed by transferring all the samples into 0.7 ml growth media for at least 24 hours. The growth media used in the experiment was a version of Dulbecco Modified Eagle Medium (DMEM) that did not have any phenol red, but with added 1 v/v % 200 mM L-Glutamine, 10 v/v % fetal bovine serum, 1 µg/ml hydrocortisone, 3 ng/ml basic fibroblast growth factor, 10 ng/mL human epidermal growth factor, 10 µg/ml heparin, 10 µg/ml gentamicin and 0.25 µg/ml amphotericin B.

Figure 15:
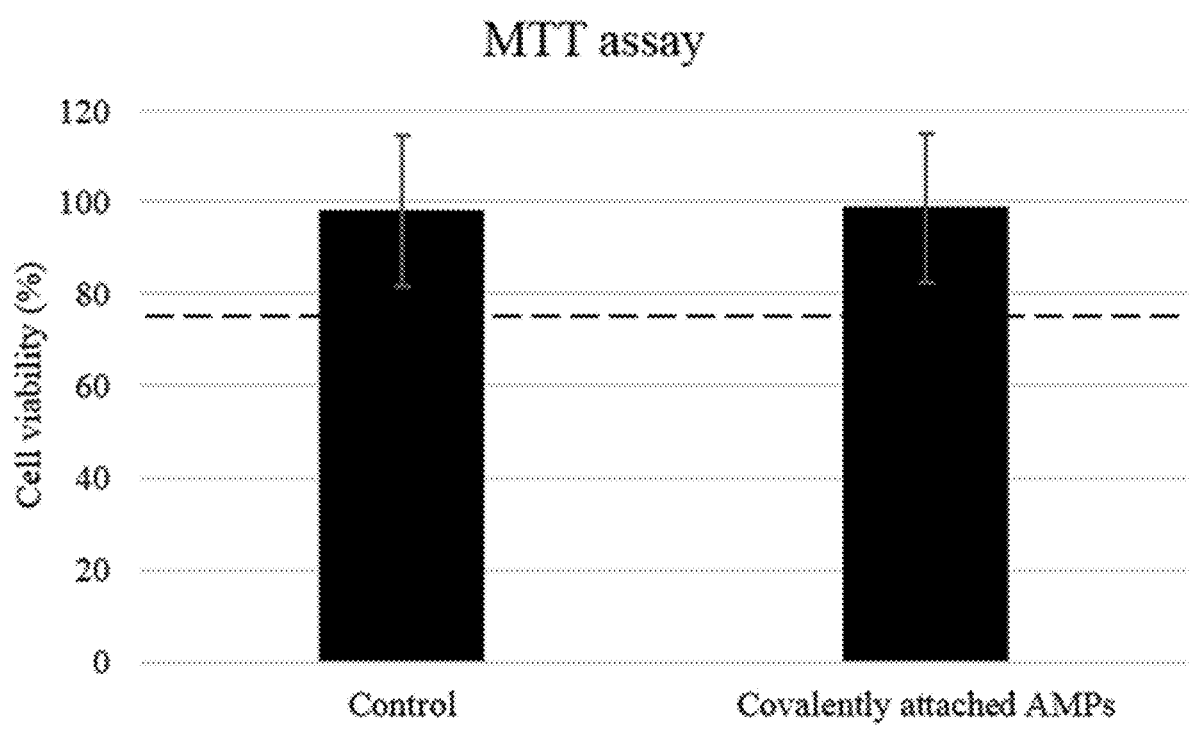
FIG. 15 shows cell viability obtained by two MTT assays performed on fibroblast with media exposed to control and test samples. The dashed line indicates 75% cell viability. Samples that are higher than this is regarded as non-toxic. The hydrogels analysed were the control and the covalently attached AMPs. The control and the antimicrobial amphiphilic hydrogel showed a significantly higher cell viability than the 75% cut-off.

While the hydrogels were in the growth media, the tubes were occasionally mixed and vortexed in order for the potentially toxic compounds to leach out from the hydrogels. 0.2 ml of each growth media was then added to separate wells of a 96-well plate together with a uniform number of human fibroblasts. The plate was placed in a humidified incubator at 37° C. and 5% CO$_2$ and the fibroblasts were expanded to 30 000-50 000 cells per well. The media was then removed and replaced by 100 µl of the corresponding sample-soaked growth media together with 10 µl of 12 mM MTT solution. A positive and a negative control was also used for the culturing. The positive control consisted of cells that were grown in a media that had not been in contact with any hydrogel sample and the negative control consisted of only growth media and the MTT solution without any cells. The plate was then incubated for 4 hours followed by the addition of 100 µl SDS-HCl solution to each well. The plate was then incubated again for 4 hours followed by absorbance measurements at 570 nm which correlates to the cell density. Results are presented in FIG. 15. The dotted line indicates 75% cell viability, which is generally regarded as the cut-off point, where values lower than this are said to be toxic to the cells. 0% on the bar would indicate no growth at all and 100% would indicate a growth equal to the positive control, which was only growth media. The results showed significant data that neither of the hydrogels released any substances that are toxic towards human fibroblasts.

3. The antimicrobial hydrogel according to claim 2, wherein the antimicrobial agent is an antimicrobial peptide.

4. The antimicrobial hydrogel according to claim 3, wherein the antimicrobial agent is an antimicrobial peptide comprising a stretch of at least one hydrophobic amino acid(s) forming a hydrophobic region for interaction with the hydrophobic regions of the hydrogel.

5. The antimicrobial hydrogel according to claim 3, wherein the antimicrobial peptide is RRP9W4N.

6. The antimicrobial hydrogel according to claim 1, wherein the amphiphilic molecule is a co-polymer.

7. The antimicrobial hydrogel according to claim 6, wherein the co-polymer is a diacrylate derivative of a triblock co-polymer.

8. The antimicrobial hydrogel according to claim 1, wherein the ordered nanostructure is an ordered and repeating nanostructure of micellar, hexagonal, cubic or lamellar morphology.

9. The antimicrobial hydrogel according to claim 1, wherein the antimicrobial agent is also physically absorbed in to the hydrogel, such that a portion of the antimicrobial agent present in the hydrogel is physically absorbed and a portion is covalently attached.

10. The antimicrobial hydrogel according to claim 1, wherein a therapeutic agent, in addition to the antimicrobial agent, is covalently attached or physically absorbed to the hydrophilic and/or hydrophobic domains of the first amphiphilic component.

11. The antimicrobial hydrogel according to claim 1, wherein the first amphiphilic component is chemically cross-linked via reactive groups present on the first amphiphilic component.

The invention claimed is:

1. A solid antimicrobial hydrogel comprising a first cross-linked amphiphilic component, said first amphiphilic component being a chemically cross-linked lyotropic liquid crystal and having an ordered nanostructure of hydrophobic and hydrophilic domains, the hydrogel comprising an antimicrobial agent covalently attached to the hydrophilic and/or hydrophobic domains.

2. The antimicrobial hydrogel according to claim 1, wherein the antimicrobial agent is a substantially amphiphilic antimicrobial agent covalently immobilized on the hydrophilic domains and, optionally, hydrophobic domains of the first amphiphilic component.

12. The antimicrobial hydrogel according to claim 1, wherein the hydrogel is substantially non-degrading in physiological conditions.

13. A device comprising a first antimicrobial hydrogel according to claim 1.

14. The device according to claim 13, wherein the first antimicrobial hydrogel is applied on a substrate.

15. The device according to claim 13, wherein the first antimicrobial hydrogel forms a first antimicrobial hydrogel layer, wherein the substrate has an increased mechanical strength relative to the first antimicrobial hydrogel layer.

16. The device according to claim 13, wherein the device is selected from the group comprising an implant, a surgical instrument, a stent, a catheter, a skin graft, a contact lens, personal hygiene articles, nappies, a wound dressing, an ostomy dressing, ostomy baseplate, incision film, surgical drape, a patch, a bandage, a band-aid, a plaster, an adhesive, an adhesive tape, an adhesive plaster, a sticking-plaster, and a court-plaster, and any combination thereof.

17. The antimicrobial hydrogel according to claim 1, or a device comprising the antimicrobial hydrogel for use in the prevention and/or treatment of burns, scars, bacterial infections, viral infections, and/or fungal infections.

18. A method of producing an antimicrobial hydrogel according to claim 1, comprising:

providing a first cross-linkable amphiphilic component, cross-linking the first amphiphilic component to form a three-dimensional solid and chemically cross-linked lyotropic liquid crystal from the first amphiphilic component, and, attaching, covalently, an antimicrobial agent to the hydrogel.

19. The method according to claim 18, wherein the antimicrobial agent is substantially localised to the surface of the hydrogel, and wherein the attaching of the antimicrobial agent is performed via surface application of a solution comprising an antimicrobial agent.

20. The method according to claim 19, wherein the antimicrobial agent is an antimicrobial peptide (AMP) and the surface application is achieved via spraying a solution having a concentration of AMP greater than about 50 μM, such as greater than about 200 μM, to the surface of the hydrogel.

21. The antimicrobial hydrogel according to claim 7, wherein the co-polymer is a derivative of poly(ethylene oxide)-poly(propylene oxide)-poly(ethylene oxide) (PEO-PPO-PEO).

* * * * *

```
SEQUENCE LISTING

<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: 13
<223> OTHER INFORMATION: AMIDATION

<400> SEQUENCE: 1

Arg Arg Pro Arg Pro Arg Pro Trp Trp Trp Trp Arg Pro
1               5                   10

<210> SEQ ID NO 2
<211> LENGTH: 13
<212> TYPE: PRT
<213> ORGANISM: Artificial Sequence
<220> FEATURE:
<223> OTHER INFORMATION: syntehtic peptide
<220> FEATURE:
<221> NAME/KEY: MOD_RES
<222> LOCATION: 13
<223> OTHER INFORMATION: AMIDATION

<400> SEQUENCE: 2

Arg Arg Pro Arg Pro Trp Trp Arg Pro Trp Trp Arg Pro
1               5                   10
```